US009945051B2

United States Patent
Ebright

(10) Patent No.: US 9,945,051 B2
(45) Date of Patent: Apr. 17, 2018

(54) COLOR-ENCODING AND IN-SITU INTERROGATION OF MATRIX-COUPLED CHEMICAL COMPOUNDS

(71) Applicant: RUTGERS, THE STATE UNIVERSITY OF NEW JERSEY, New Brunswick, NJ (US)

(72) Inventor: Richard Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 413 days.

(21) Appl. No.: 14/607,496

(22) Filed: Jan. 28, 2015

(65) Prior Publication Data

US 2015/0233934 A1      Aug. 20, 2015

Related U.S. Application Data

(63) Continuation of application No. 11/407,016, filed on Apr. 19, 2006, now abandoned, which is a
(Continued)

(51) Int. Cl.
*C40B 20/04* (2006.01)
*C40B 50/04* (2006.01)
(Continued)

(52) U.S. Cl.
CPC ............. *C40B 20/04* (2013.01); *C40B 50/04* (2013.01); *C40B 50/16* (2013.01); *G01N 21/29* (2013.01);
(Continued)

(58) Field of Classification Search
CPC ......... C40B 20/04; C40B 50/16; C40B 50/04; C40B 70/00; G01N 21/64; G01N 21/29;
(Continued)

(56) References Cited

U.S. PATENT DOCUMENTS 3,982,182 A   9/1976 Hogg
4,456,513 A   6/1984 Kawai et al.
(Continued)

FOREIGN PATENT DOCUMENTS

EP   0269764   6/1988
EP   0478319   4/1992
(Continued)

OTHER PUBLICATIONS

Ohlmeyer et al. (Proc. Natl. Acad. Sci., 1993, 90:10922-10926).*
(Continued)

*Primary Examiner* — Jeremy C Flinders
(74) *Attorney, Agent, or Firm* — Robert C. Netter, Jr.; Dann, Dorfman, Herrell & Skillman

(57) ABSTRACT

A method and apparatus for the physico-chemical encoding of a collection of beaded resin ("beads") to determine the chemical identity of bead-anchored compounds by in-situ interrogation of individual beads. The present invention provides method and apparatus to implement color-coding strategies in applications and including the ultrahigh-throughput screening of bead-based combinatorial compounds libraries as well as multiplexed diagnostic and environmental testing and other biochemical assays.

4 Claims, 12 Drawing Sheets

Related U.S. Application Data continuation of application No. 09/448,420, filed on Nov. 22, 1999, now Pat. No. 7,083,914, which is a continuation of application No. PCT/US98/10719, filed on May 22, 1998.

(60) Provisional application No. 60/047,472, filed on May 23, 1997.

(51) Int. Cl.
*C40B 50/16* (2006.01)
*G01N 21/64* (2006.01)
*G01N 33/58* (2006.01)
*G01N 21/29* (2006.01)
*C40B 40/10* (2006.01)
*C40B 40/06* (2006.01)
*C40B 70/00* (2006.01)
*G01N 21/17* (2006.01)

(52) U.S. Cl.
CPC ........... *G01N 21/64* (2013.01); *G01N 33/582* (2013.01); *C40B 70/00* (2013.01); *G01N 21/6458* (2013.01); *G01N 2021/1765* (2013.01)

(58) Field of Classification Search
CPC ......... G01N 33/582; G01N 33/216458; G01N 2021/1765
See application file for complete search history.

(56) References Cited

U.S. PATENT DOCUMENTS

| | | |
|---|---|---|
| 4,499,052 A | 2/1985 | Fulwyler |
| 4,647,544 A | 3/1987 | Nicoli et al. |
| 4,717,655 A | 1/1988 | Fulwyler |
| 4,767,205 A | 8/1988 | Schwartz et al. |
| 4,822,746 A | 4/1989 | Walt |
| 4,994,373 A | 2/1991 | Stavrianopoulos et al. |
| 5,002,867 A | 3/1991 | Macevicz |
| 5,028,545 A | 7/1991 | Soini |
| 5,105,305 A | 4/1992 | Betzig |
| 5,114,864 A | 5/1992 | Walt |
| 5,132,097 A | 7/1992 | Van Deusen et al. |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,306,618 A | 4/1994 | Prober et al. |
| 5,320,814 A | 6/1994 | Walt et al. |
| 5,362,653 A | 11/1994 | Carr et al. |
| 5,405,784 A | 4/1995 | Van Hoegaerden |
| 5,480,723 A | 1/1996 | Klainer et al. |
| 5,496,997 A | 3/1996 | Pope |
| 5,512,490 A | 4/1996 | Walt et al. |
| 5,565,324 A | 10/1996 | Still et al. |
| 5,567,627 A | 10/1996 | Lehnen |
| 5,573,909 A | 11/1996 | Singer et al. |
| 5,585,069 A | 12/1996 | Zanzucchi et al. |
| 5,593,838 A | 1/1997 | Zanzucchi et al. |
| 5,633,724 A | 5/1997 | King et al. |
| 5,633,972 A | 5/1997 | Walt et al. |
| 5,650,489 A | 7/1997 | Lam et al. |
| 5,652,059 A | 7/1997 | Margel |
| 5,674,698 A | 10/1997 | Zarling et al. |
| 5,690,894 A | 11/1997 | Pinkel et al. |
| 5,700,897 A | 12/1997 | Klainer et al. |
| 5,723,218 A | 3/1998 | Haugland et al. |
| 5,728,529 A | 3/1998 | Metzeker et al. |
| 5,744,305 A | 4/1998 | Fodor et al. |
| 5,770,445 A | 6/1998 | Cargill et al. |
| 5,779,976 A | 7/1998 | Leland et al. |
| 5,807,755 A | 9/1998 | Ekins |
| 5,814,524 A | 9/1998 | Walt et al. |
| 5,837,551 A | 11/1998 | Ekins |
| 5,874,219 A | 2/1999 | Rava et al. |
| 5,939,021 A | 8/1999 | Hansen et al. |
| 5,961,923 A | 10/1999 | Nova et al. |
| 5,965,452 A | 10/1999 | Kovacs |
| 5,968,736 A | 10/1999 | Still et al. |
| 5,981,180 A | 11/1999 | Chandler et al. |
| 5,989,835 A | 11/1999 | Dunlay et al. |
| 6,023,540 A | 2/2000 | Walt et al. |
| 6,048,690 A | 4/2000 | Heller et al. |
| 6,083,763 A | 7/2000 | Balch |
| 6,090,545 A | 7/2000 | Wohlstadter et al. |
| 6,090,912 A | 7/2000 | Lebl et al. |
| 6,200,737 B1 | 3/2001 | Walt et al. |
| 6,251,691 B1 | 6/2001 | Seul |
| 6,266,459 B1 | 7/2001 | Walt et al. |
| 2006/0188943 A1 | 8/2006 | Seul et al. |

FOREIGN PATENT DOCUMENTS

| | | |
|---|---|---|
| EP | 0723146 | 7/1996 |
| WO | 8911101 | 11/1989 |
| WO | 9302360 | 2/1993 |
| WO | 9306121 | 4/1993 |
| WO | 9324517 | 12/1993 |
| WO | 9512808 | 5/1995 |
| WO | 9607917 | 3/1996 |
| WO | 9714028 | 4/1997 |
| WO | 9740383 | 10/1997 |
| WO | 9806007 | 2/1998 |
| WO | 9853300 | 11/1998 |
| WO | 9918434 | 4/1999 |
| WO | 9919515 | 4/1999 |

OTHER PUBLICATIONS

Egner et al. (Chem. Comm., 1997, pp. 735-736).*
Microsphere Selection Guide, Bangs Laboratories, Inc, 1998, Fisher, IN.
Gordon et al., "Applications of Combinatorial Technologies to Drug Discovery. 2. Combinatorial Organic Synthesis, Library Screening Strategies, and Future Directions", J. Med. Chem., 1994, 37:1385-1401.
Peterson et al., "Fiber optic pH probe for physiological use", Anal. Chem, 1980, 53(6):864-869.
Peterson et al., Fiber Optic Sensors for Biomedical Applications, Science, 1984, 123-127, 13.
Fuh et al., "Single Fibre Optic Fluorescence pH Probe", The Analyst, 1987, 112:1159-1163.
Nielson et al., "Solid-Phase Synthesis of Small Molecule Libraries using Double Combinatorial Chemistry", Tetrahedron Letters, 1997, 38(11):2011-2014.
Nagayama et al., Phase Transitions, 1993, 185-203, 45.
Campian et al., Colored and Fluorescent Solid Supports, Innovation and Perspectives in Solid-phase Synthesis, 1994, 469-472, Ed: E. Birmingham, Mayflower, London.
Bangs Immunological Applications of Microsphers, The Latex Course, 1996, Bangs Laboratories.
Fluorescent Microspheres (Tech Note #19), 1997, Bangs Laboratories.
Grazia et al., "In-Vivo Biomedical Monitoring by Fiber Optic Systems", J. Lightwave Tech., 1995) 13:1396-1406.
Boyce et al., "Peptidosteroidal Receptors for Opioid Peptides. Sequence-Selective Binding Using a Synthetic Receptor Library" J. Am. Chem. Soc., 1994, 116(17):7955-7956.
Barnard et al., "A fibre-optic chemical sensor with discrete sensing sites" Nature, 1991, 353:338-340.
Pope, E.J.A., "Fiber optic chemical microsensors employing optically active silica microspheres" SPIE, 1995, 2388:245-256.

(56) References Cited

OTHER PUBLICATIONS

Fulton et al., "Advanced multiplexed analysis with the FlowMetrixTM system" Clin. Chem., 1997, 43(9):1749-1756.
Healey et al., "Fiberoptic DNA Sensor Array Capable of Detecting Point Mutations", Anal. Biochem., 1997, 251:270-279.
Houghton, R.A., "General method for the rapid solid-phase synthesis of large numbers of peptides: Specificity of antigen-antibody interaction at the level of individual amino acids" Proc. Natl. Acad. Sci., 1985, 82:5131-5135.
Micheletto, et al., "A Simple Method for the Production of a Two-Dimensional, Ordered Array of Small Latex Particles", Langmuir, 1996, 11:3333-3336.
Roberts et al., "Patterned Magnetic Bar Array for High-Throughput DNA Detection" IEEE Trans. Magnetics, 2004, 40:3006-3008.
Scott, et al., "Properties of Fluorophores on Solid Phase Resins; Implications for Screening, Encoding and Reaction Monitoring" Bioorganic & Medicinal Chemistry Letters, 1997, 7(12):1567-1572.
Kuo, et al., "Force of single kinesin molecules measured with optical tweezers", Science, 1993, 260(5105):232-4.
Matsushita, et al., "Distribution of Components in Composite Two-Dimensional Arrays of Latex Particles and Evaluation in Terms of the Fractal Dimension", Langmuir, 1997, 13(9):2582-2584.
Molecular Probes webpage snapshot from Jan. 1998.
Southwick, et al., "Cyanine dye labeling reagents—carboxymethylindocyanine succinimidyl esters", Cytometry, 1990, 11:418-430.
Mullins, J.M., "Overview of Fluorophores", Methods in Molecular Biology, 1994, 34:107-116.
Adams, et al., "A Reinvestigation of the Preparation, Properties, and Applications of Aminomethyl and 4-Methylbenzhydrylamine Polystyrene Resins", J. Org. Chem., 1998, 63:3706-3716.

\* cited by examiner

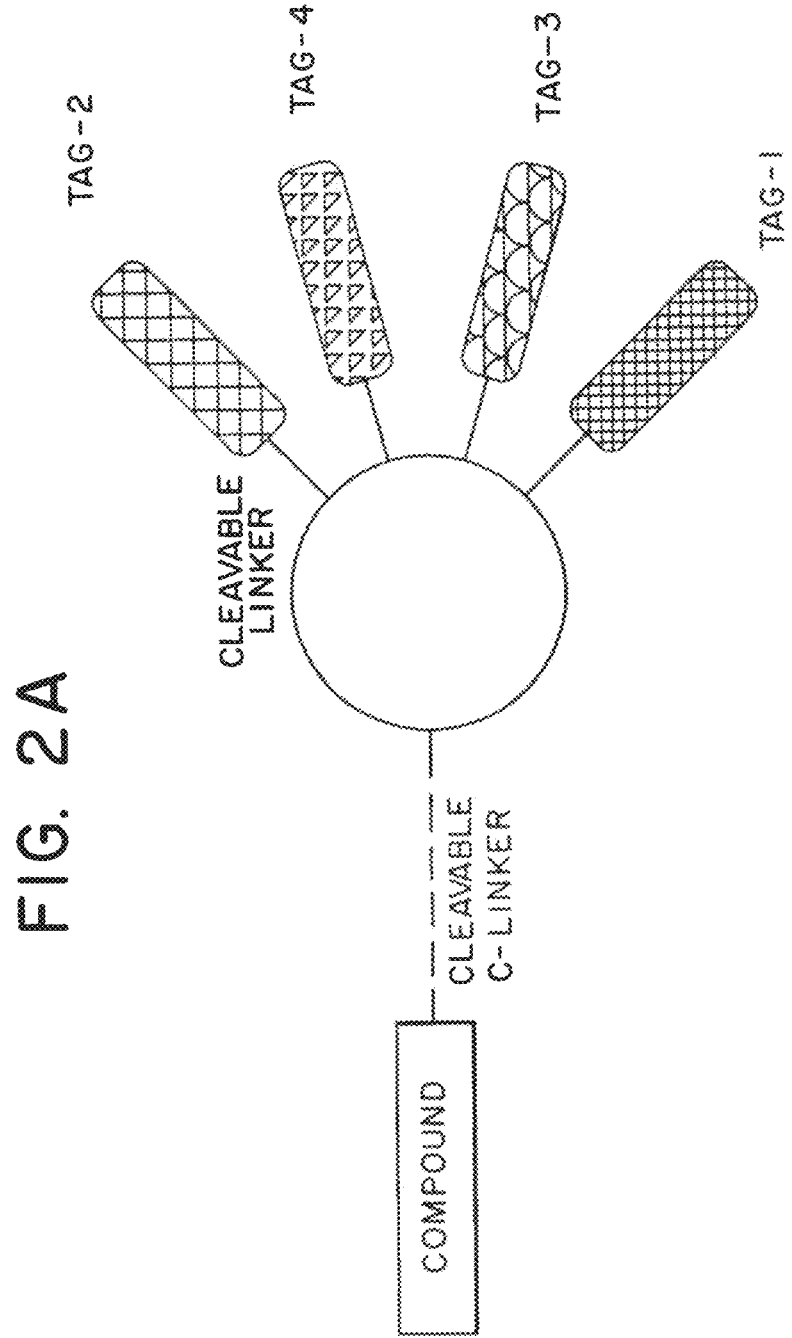

STEP 1 → STEP 2

STEP 1 → STEP 2

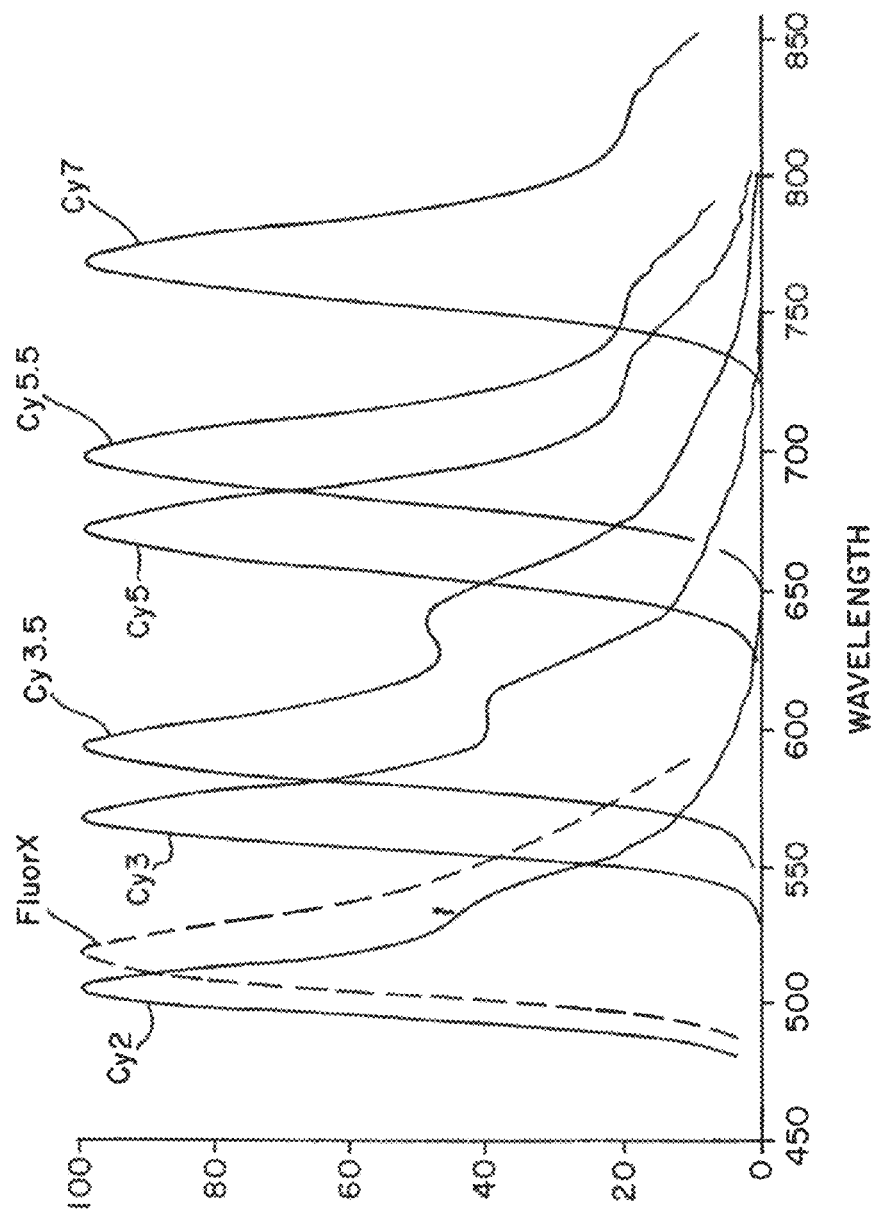

FIG. 5B

| Fluorophore | Color of Fluorescence | Absorption Maximum (nm) | Fluorescence Maximum (nm) | Extinction Coefficient ($M^{-1}cm^{-1}$) | Quantum Yield for Protein Conjugates | Formula Weight (daltons) | |
|---|---|---|---|---|---|---|---|
| | | | | | | Bisfnc. | Monofnc. |
| Cy2 | Green | 489nm | 506nm | ~150,000 | >0.12 | 896.95 | 713.78 |
| Cy3 | Orange | 550nm | 570nm | 150,000 | >0.15 | 949.11 | 765.95 |
| Cy3.5 | Scarlet | 581nm | 596nm | 150,000 | >0.15 | 1285.54 | 1102.37 |
| Cy5 | Far-Red | 649nm | 670nm | 250,000 | >0.28 | 975.15 | 791.99 |
| Cy5.5 | Near IR | 675nm | 694nm | 250,000 | >0.28 | 1311.58 | 1128.41 |
| Cy7 | Near IR | 743nm | 767nm | ~250,000 | ~0.28 | 1001.19 | 818.02 |
| FluorX | Green | 494nm | 520nm | 68,000 | 0.3 | | 586.60 |

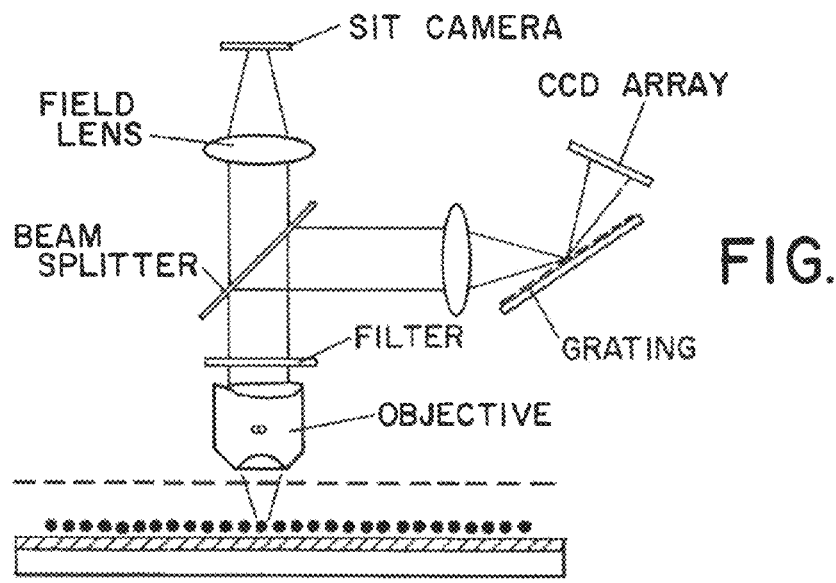
FIG. 7
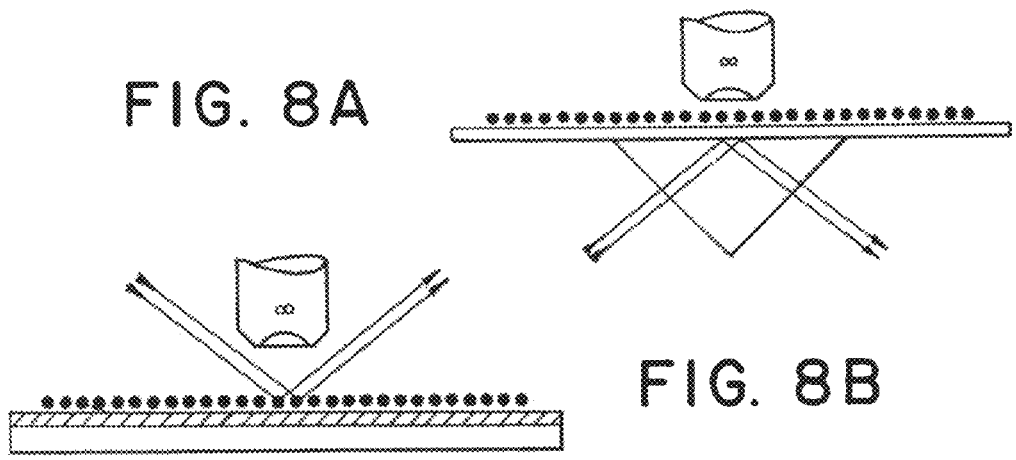
FIG. 8A
FIG. 8B
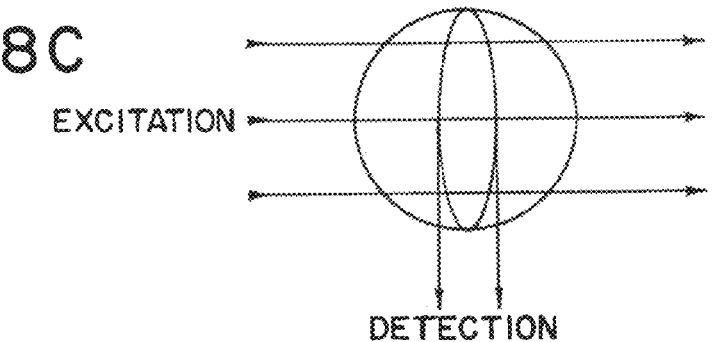
FIG. 8C

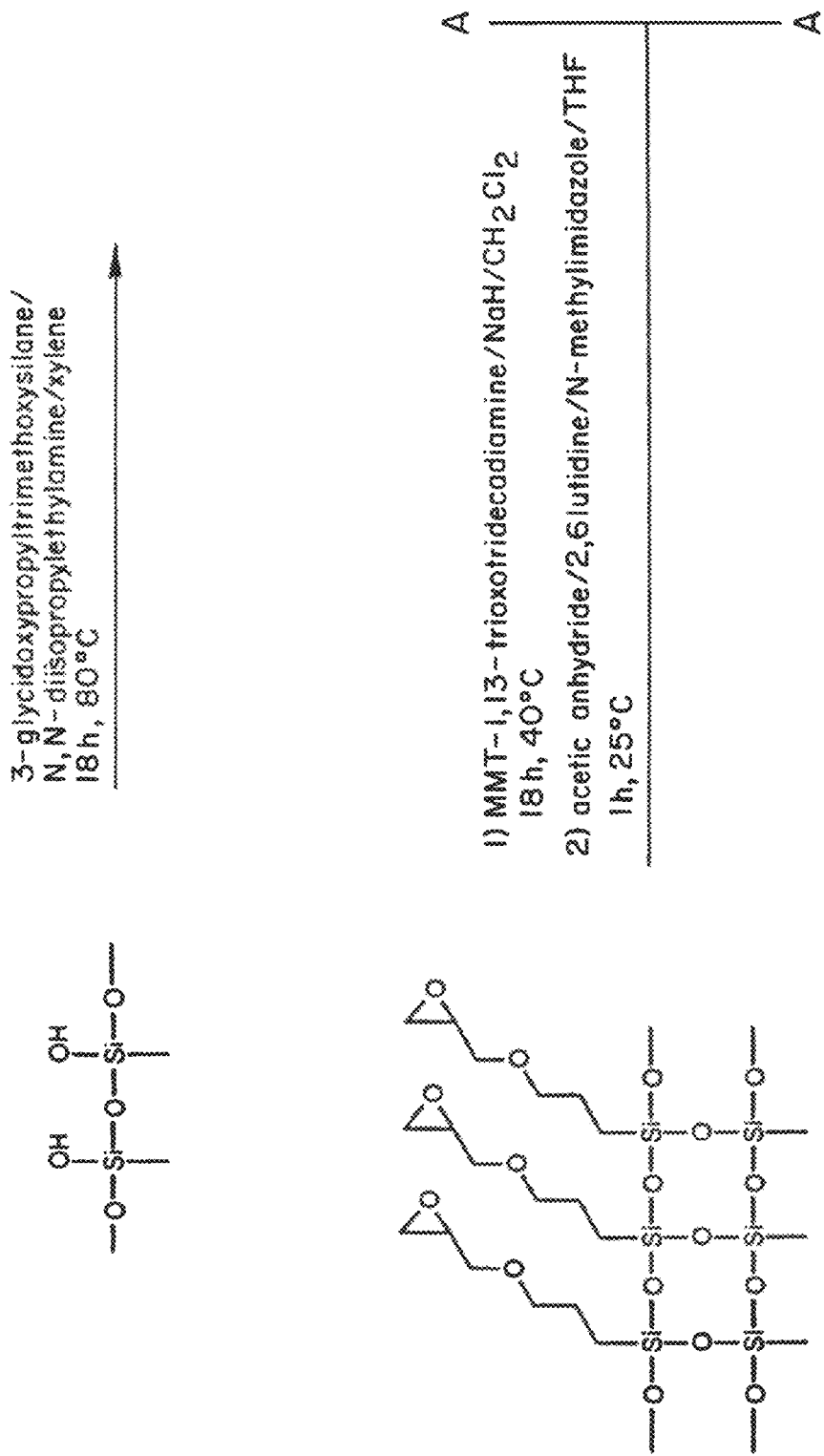

COLOR-ENCODING AND IN-SITU INTERROGATION OF MATRIX-COUPLED CHEMICAL COMPOUNDS

CROSS-REFERENCE TO RELATED APPLICATIONS

This application is a continuation application of U.S. patent application Ser. No. 11/407,016, filed Apr. 19, 2006, which is a continuation of application Ser. No. 09/448,420, filed Nov. 22, 1999, now U.S. Pat. No. 7,083,914, which is a continuation of International Application PCT/US98/10719, filed May 22, 1998, which claims the priority of U.S. Provisional Application Ser. No. 60/047,472, filed May 23, 1997. The entire disclosures of the aforementioned applications are incorporated herein by reference.

FIELD OF THE INVENTION

The present invention generally relates to the field of analytical chemistry.

The present invention specifically relates to a highly parallel mode of presenting and probing multiple chemical compounds, with applications to combinatorial library synthesis, ultrahigh-throughput screening, diagnostic assays for multiple agents and sensors. The present invention introduces several color codes to label collections of carrier particles such as colloidal beads; in addition, the present invention describes a method and apparatus for the in-situ interrogation of beads or collections of beads by way of multi-color fluorescence imaging and spectral analysis of individual beads to ascertain the chemical identities of bead-anchored compounds. The encoding of beads by simple and extended simple color codes and by binary and extended binary color codes may be augmented by measuring bead size and shape or other physico-chemical properties such as polarizability embedded in the bead core.

BACKGROUND OF THE INVENTION

1—Solid Phase Chemical Libraries

An emerging paradigm for lead discovery in pharmaceutical and related industries such as agricultural biotechnology, is the assembly of novel synthetic compound libraries by new methods of solid state "combinatorial" synthesis. Combinatorial chemistry refers to a set of strategies for the parallel synthesis and testing of multiple compounds or compounds mixtures, either in solution or in solid supports in the form of beaded resins ("beads"). In general, a combinatorial synthesis employing M precursors in each of N reaction steps produces M^N compounds. For example, a combinatorial synthesis produces 4^N oligonucleotides in N steps, each employing 4 oligonucleotide precursors; similarly, a combinatorial synthesis of N steps, each employing 20 amino acid precursors, produces 20^N oligopeptides.

1.1—One Bead/One Compound Chemical Libraries

One implementation of combinatorial synthesis that is suitable to produce very large chemical libraries relies on solid supports in the form of beaded resins ("beads") and encodes reaction steps in a "divide, couple and recombine" (DCR) strategy (FIG. 1), also referred to as "resin-splitting" synthesis. The resulting "one bead/one compound" chemical libraries contain from 10^6 to 10^8 compounds. These libraries are screened by performing a wide variety of chemical and biochemical assays to identify individual compounds eliciting a positive response. The chemical identity of such compounds can be determined by direct analysis.

Two methods of direct analysis are micro-sequencing and mass spectrometry. Both methods require the physical isolation of synthesis beads displaying compounds of interest and both require off-line chemical analysis based on substantial amounts of compound—tens to hundreds of picomoles. Micro-sequencing, limited to libraries of oligopeptides and oligonucleotides, does not distinguish between stereoisomers. Mass spectrometry is unable to distinguish between precursors of equal mass such as D- and L-amino acids or leucine and isoleucine. The requirement of direct chemical analysis for a substantial quantity of compound dictates the use of large bead resins (a typical bead diameter is 130 μm) to ensure that picomolar quantities of each compound can be recovered, even when it is becoming increasingly desirable to perform high throughput screening of the compound library in miniaturized environments to reduce requisite volumes of sample and reagents and to enhance throughput.

1.2—Encoded One Bead/One Component Chemical Libraries

One approach to overcoming the serious limitations of standard one bead/one compound chemical libraries is to encode chemical compound identities. This facilitates the identification of compounds not amenable to direct determination by micro-sequencing or mass spectrometry. One encoding method employs the co-synthesis of peptides and oligonucleotides to represent the identity of non-sequenceable synthesis products (Nikolaiev et al., "Peptide-Encoding for Structure Determination of Non-Sequenceable Polymers Within Libraries Synthesized and Tested on Solid-Phase Supports", Peptides Res. 6, 161 (1993), the contents of which are included herein by reference). A second method, compatible with a wider range of chemical reaction conditions, employs a set of tagging molecules to record the reaction histories of beads.

One implementation of the latter method uses a set of pre-synthesized, chromatographically distinguishable molecular tags T1, T2, . . . , TM to construct a chemical binary code. In prior art, molecular tags are structurally related molecules (FIG. 2) which can be identified by their characteristic gas chromatographic retention times (Still et al., "Complex combinatorial libraries encoded with tags", U.S. Pat. No. 5,565,324, the contents of which are included herein by reference).

At each step of DCR synthesis, a unique tag from the set is added to each divided aliquot to record the reaction carried out with that aliquot. The concept may be illustrated by examining the steps of a 2-step synthesis using reagents $R^1_1$, $R^1_2$ and $R^1_3$ in step 1, and reagents $R^2_1$, $R^2_2$ and $R^2_3$ in step 2, to generate nine products. The reagents of the first step are uniquely identified by the binary addresses 01 ($R^1_1$), 10($R^1_2$) and 11($R^1_3$), and the reagents of the second step are uniquely identified by the binary addresses 01($R^2_1$), 10($R^2_2$) and 11($R^2_3$). Each binary address is chemically represented in terms of a set of molecular tags: T1 (01 in step 1 representing $R^1_1$), T2 (10 in step 1 representing $R^1_2$) and T2T1 (11 in step 1 representing $R^1_3$) and analogously with T3 (01 in step 2 representing $R^2_1$), T4 (10 in step 2 representing $R^2_2$) and T4T3 (11 in step 2 representing $R^2_3$).

A sequence of reaction steps is recorded by simply concatenating binary addresses. Thus, 11.01, read right to left, would indicate the sequence "reagent $R^2_3$ in step 2, reagent $R^1_1$ in step 1". The chemical representation of this sequence is T4T3.T1, and the presence on the bead of this particular set of tags indicates the chemical identity of the bead-anchored synthesis product. The strategy is readily generalized to larger reactions. For example, 7 reagents to be used in each reaction step can be uniquely identified by the binary addresses 001($R^1_1$), 010($R^1_2$), . . . , 111($R^1_7$). Although superior to un-encoded one bead/one compound methods, nevertheless the tagging strategy of prior art still suffer from three limitations. First, individual beads of interest must be physically isolated from the rest; next, molecular tags must be chemically or photochemically cleaved from the bead and cleaved tags must be collected; and finally, chemical analysis (e.g., gas chromatography) must be performed. These numerous time- and labor-intensive manipulations eliminate much of the enhancement in throughput gained by the DCR synthesis strategy.

1.3 Screening and Lead Compound Optimization

The high specificity of typical biological substrate-target interactions implies that the vast majority of compounds in a library will be inactive for any particular target. Thus, the task of screening is to identify the very few compounds within the library that display activity in binding or in functional assays. Common targets include enzymes and receptors as well as nucleic acids.

To implement the rapid screening and scoring of an entire library of synthetic compounds, in practice containing $10^4$ to $10^8$ compounds, requires systematic screening procedures if the task is to be completed within viable time frames. Several assay formats have been described to implement the screening of bead-based combinatorial libraries. These include: reaction of a collection of beads, allowed to settle under gravity, with an enzyme-labeled or fluorophore-labeled target molecule followed by visual detection (Lam et al., "A new type of synthetic peptide library for identifying ligand-binding activity", Nature 354 (1991), the contents of which are included herein by reference); incubation of beads with radio-labeled target molecules and subsequent agarose immobilization of beads and auto-radiographic detection (Kassarjian, Schellenberger and Turck, "Screening of Synthetic Peptide Libraries with Radio-labeled Acceptor Molecules", Peptide Res. 6, 129 (1993), the contents of which are included herein by reference); and partial release of compounds from beads for solution-phase testing (Salmon et al., "Discovery of biologically active peptides in random libraries: Solution-phase testing after staged orthogonal release from resin beads", Proc. Natl. Acad. Sc. USA 90, 11708 (1993), the contents of which are included herein by reference).

WO95/32425 provides a method of preparing combinational libraries using a method of encoding combinational libraries with fluorophore labeled beads. According to the method, a first combinational library is prepared by conducting a set of reactions on tagged beads to afford an encoded first registry (i.e., step in the synthetic sequence). A second combinational library is prepared using similar reaction steps but the tagged beads are combined and separated prior to the first reaction sequence and the beads are sorted prior to the second reaction sequence. Subsequent libraries are prepared as for the second library except that the sorting step takes place prior to a different registry in each subsequent library. Thus, WO95/32425 teaches only individually labelling the first step and physical separatois of beads to identify each modified combinational library.

Nederlof et al., Cytometry, 13, 839-845 (1992), teaches the use of ratio labeling as a way of increasing the number of simultaneously detectable probes beyond the seven used previously. In this approach, ratio-labelled probes are identified on the basis of the ratio of color intensity, not just the particular colors used. Fluorescence ratios are measured and used as additional encoding colors. The method requires double-labeling of probes using different ratios of labels. The method is not specifically directed to synthetic combinational libraries. Accordingly, the field of Nederlof's method is the detection of multiple DNA/RNA sequence by in situ hybridization, and is not relevant to the field of encoding of synthetic chemical libraries.

Speiche, Ballard & Ward, Nature Genetics, 12, 368 (1996), describe a method of characterizing complex chromosomal karyo types using multi-fluorescence in situ hybridization. Instead of using ratio-double labelling as in Nederlof, Speiche et al. use a set of six fluorescent dyes with spectral emission peaks spread across the photometric response range to visualize 27 combinationally labelled probes. Speiche et al. do not disclose a method of encoding synthetic combinational libraries.

Still et al., Proc. Nat'l Acad. Sci., 90, 10922-926 (1993), disclose a method of synthesis of tagged combinational libraries using a binary code based on different electrophoric tags. The method requires use of photocleavable molecular tags which comprise variously substituted aryl moieties linked via a variable-length aliphatic hydrocarbon chain, whereby the tags when cleaved are distinctly resolvable by capillary gas chromatography with electochemical detection. Color detection is not used in this method. The method also requires cleavage from the solid support in order to analyze the sequence. In related work, Still et al. U.S. Pat. No. 5,721,099 disclose methods of preparing encoded combinatorial libraries, but again the method requires cleavage of the identifier tags prior to analysis of the encoded reaction history. In contrast, the present invention provides an in situ approach to the interrogation of encoded combinatorial libraries, and represents an advance over the prior methods of encoding libraries. The success of the present invention is unexpected in view of the prior approaches because of the scattering phenomena expected for a spectral analysis performed in heterogeneous media which would dissipate spectral signal-to-noise giving rise to practical difficulties in detecting accurately relative abundance information for fluorophore tags. The present methodology demonstrates for the first time a way of solving these practical problems in performing in situ encoding and interrogation of combinatorial libraries.

II—Multi-Agent Monitoring and Diagnostics

Diagnostic panels display multiple chemistries to screen unknown solutions for the presence of multiple agents. For example, blood group specificity is determined by spotting an unknown blood sample onto a panel of surface-bound antibodies whose arrangement in the panel reflects their antigen-specificity. Antigen-binding to any specific patch in the panel reveals the chemical identify of the antigen and enhance the blood type. Another realization of the same concept of displaying multiple diagnostic probes in a spatially encoded panel or array involves screening of mutations by assaying for hybridization of DNA to one of a large number of candidate matching strands which are placed in known positions on a planar substrate in a checkerboard pattern. This may be achieved by dispensing droplets containing distinct probes, or may involve the in-situ synthesis of oligonucleotide strands of varying composition.

Spatial encoding relies on the panel or array fabrication process to preserve chemical identity, adding time and expense. As the number of fields in the checkerboard increases, so does the challenge of fabricating the requisite array. In addition, probes must be immobilized—usually by adhesion to the surface of a planar substrate—to maintain the integrity of the spatial encoding scheme. In practice, this assay format can be problematic: sample accumulation can be slow and probe accessibility restricted.

III—Current Applications of Multicolor Fluorescence Detection

The present invention describes a method and apparatus for in-situ interrogation and deconvolution of bead-based combinatorial libraries using multi-color fluorescence imaging and spectral analysis. Recent applications of multi-color fluorescence spectroscopy to DNA sequencing and chromosome painting place requirements on sensitivity and wavelength selectivity exceeding those encountered in conventional applications such as determinations of fluorescence intensity ratios.

Within the context of DNA sequencing, a variety of configurations for rapid detection of 4-color fluorescence have been described. These involve: a dedicated photomultiplier tube detector for each emission wavelength, with corresponding sets of beam splitters in the optical path to produce spatially separated beams; a single detector and rotating filter wheel to select the desired set of wavelengths in a multiplexed recording mode; or a dispersive arrangement that relies on a prism or grating to split the emitted light from multiple fluorophores according to wavelength and takes advantage of recent advances in charge-coupled device (CCD) technology to record spectra on an integrating linear of rectangular CCD array (Karger et al., "Multiwavelength fluorescence detection for DNA sequencing using capillary electrophoresis", Nucl. Acids Res. 19, 4955 (1991), the contents of which are incorporated herein by reference).

SUMMARY OF THE INVENTION

The present invention provides a method to construct several color codes for the purpose of uniquely labeling members of a group of beads or equivalent objects ("beads") to preserve the chemical identity of the beads and thus the identity of bead-coupled chemical compounds. These color codes are based on a set of encoding fluorophores of distinguishable wavelengths, excited-state lifetimes and levels of intensity, the latter controlled by adjusting the abundances of dyes. Specifically, the present invention describes a method and apparatus for the encoding and in-situ interrogation of a set of distinct, bead-based chemistries.

Binary and extended binary color codes offer large coding capacity and represent a general strategy to encode multistep reaction histories such as those encountered in divide-couple-recombine (DCR) synthesis strategies for combinatorial chemical libraries, as illustrated and discussed herein.

Simple and extended simple color codes offer an efficient strategy to encode a smaller set of distinct chemistries that are typical of panels displaying multiple targets or probes in biochemical assays including multi-agent diagnostic and environmental tests and other biochemical assays.

All color codes can be augmented by varying distinguishable features of beads such as shape and size or other suitable physico-chemical parameter associated with bead cores such as polarizability.

The identity of the compound anchored to any specific bead is determined in-situ by optically probing individual beads to read the color code, as descried herein. This ensures the identification of bead-anchored chemical compounds without the need for physical separation and without the need for off-line chemical analysis.

The encoding strategy of the present invention is compatible with all formats of bead-based combinatorial synthesis and screening described to date. A preferred implementation that has the advantage of enabling miniaturization and automation of screening and decoding operations relies on planar bead arrays which may be formed, maintained and manipulated adjacent to a planar electrode surface.

BRIEF DESCRIPTION OF THE DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which:

FIG. 5A is an illustration of emission spectra of the CyDye family of commercially available fluorescent dyes whose spectral characteristics are summarized in the table (FIG. 5B) accompanying the figure (Amersham LIFE SCIENCE, Catalog of Multicolor Fluorescent Reagents, 1995, the contents of which are included herein by reference);

FIG. 7 is an illustration of a multi-color fluorescence microscope with integrated spectral analysis based on dispersive optics;

FIGS. 8A, 8B, and 8C are illustrations of several geometries of multi-color fluorescence imaging and spectrometry.

FIGS. 9A, 9B, and 9C are illustrations of an example of a solid support having a hydroxy functional group at its surface which is modified by a linker which is formed in a multistep process involving a deprotection of an Mmt protecting group and subsequent reaction with an activated ester of a fluorescent dye in accord with the present invention.

DETAILED DESCRIPTION OF THE PREFERRED EMBODIMENT

Implementation of Color Codes

The color coding strategy of the present invention provides a method to place a set of fluorophores—or, more generally, chromophores—on each bead so as to uniquely encode the chemical identity of the compound on that bead. Specifically, during each coupling step in the course of DCR combinatorial synthesis, one or more fluorophores are attached to each bead. Decoding is based on the determination of relative abundances of fluorophores on a bead of interest by in-situ optical interrogation.

Figure 1:
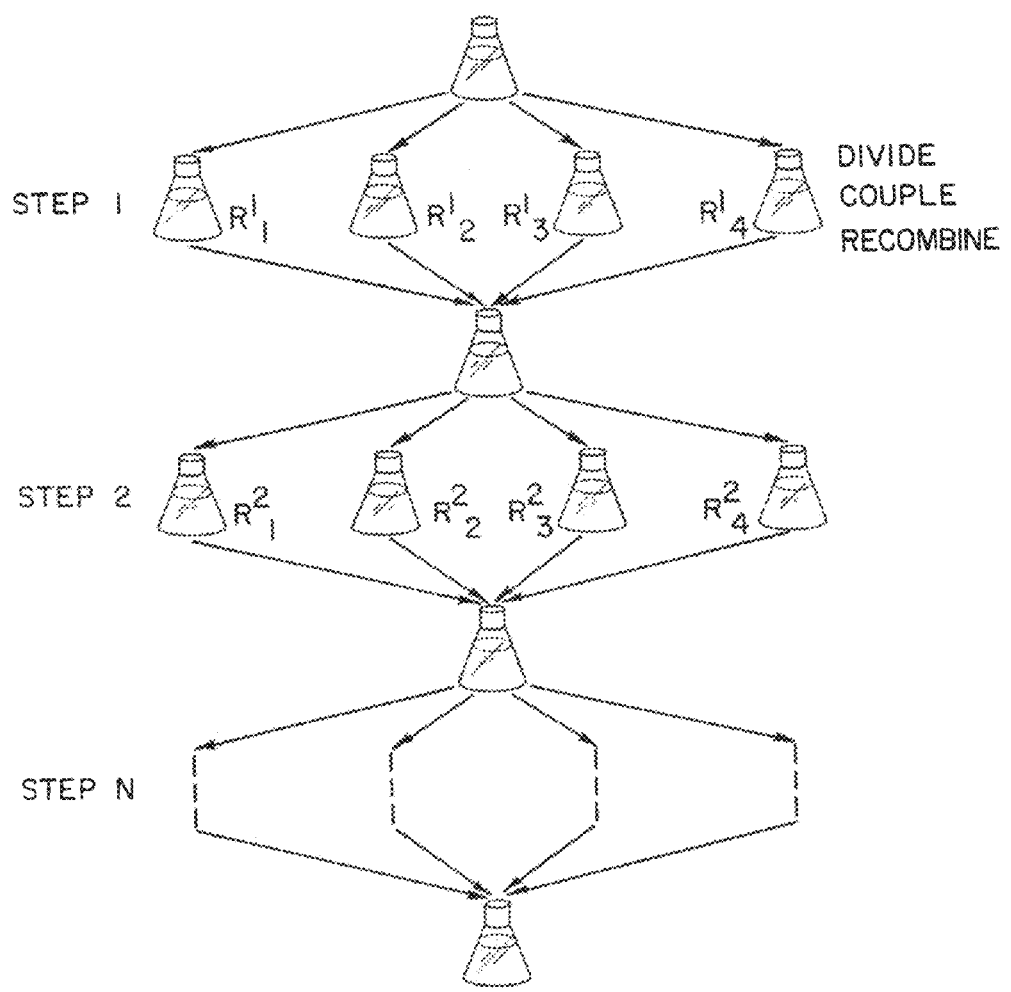
FIG. 1 is an illustration of "Divide-Couple-Recombine" combinatorial synthesis.
Figure 2B:
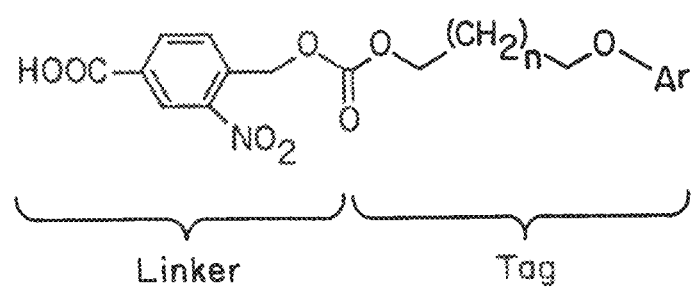
FIG. 2A is an illustration of labeling individual synthesis beads with chemical tags ("bar codes"). Examples of molecular structures used for such tags are also shown (FIGS. 2B and 2C): different tags are made by varying n and Ar.
Figure 2C:
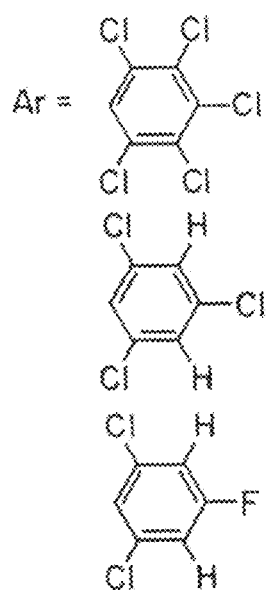
Figure 3A:
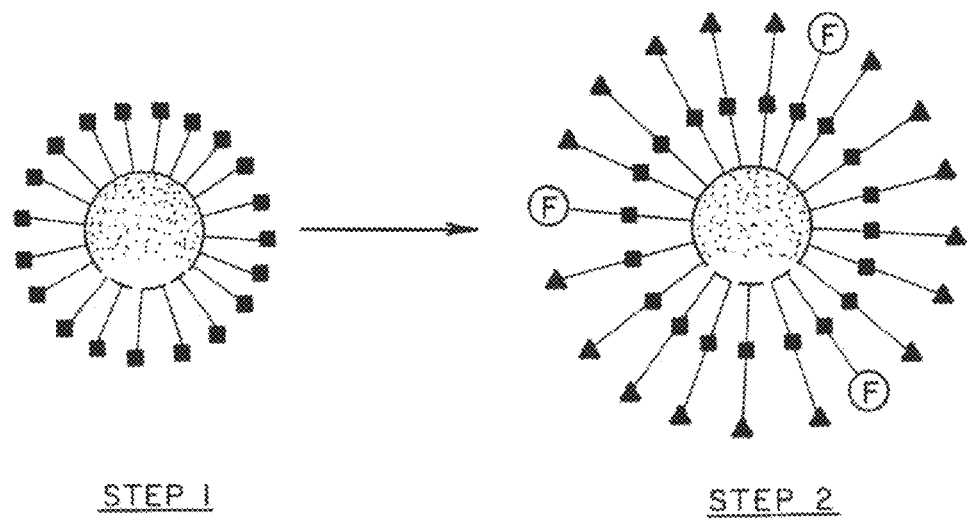
FIGS. 3A and 3B are illustrations of two alternative methods of placing fluorophore or chromophore tags (F) on synthesis beads.
Figure 3B:
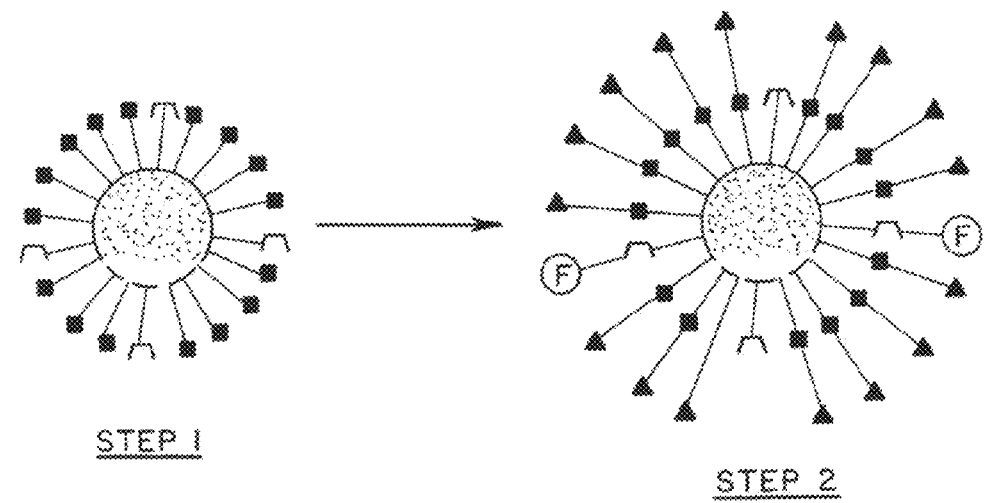

Fluorophores can be added in two ways. In the first method, the fluorophore is added directly to a small fraction of the nascent compound, thereby terminating further synthesis of that fraction of nascent compound (FIG. 3A). In the second method, the label is covalently attached to reserved reaction sites other than nascent compound to ensure that precursors are not terminated by labeling (FIG. 3B). In the first method and in most implementations of the second method, the quantity, x, of fluorophore added to each bead is sub-stoichiometric with respect to nascent compound, with x typically in the range 0.001 to 0.1 mole equivalents of nascent compound on the bead. Three factors govern the choice of x. First, the density of tags on beads must not materially interfere with synthesis and with subsequent screening assays. Second, the density of tags on beads must remain sufficiently low as to avoid complication due to fluorescence energy transfer. Third, labeled sites must be present in sufficient number to meet the requirements of signal detection and discrimination, as discussed herein.

Figure 4:
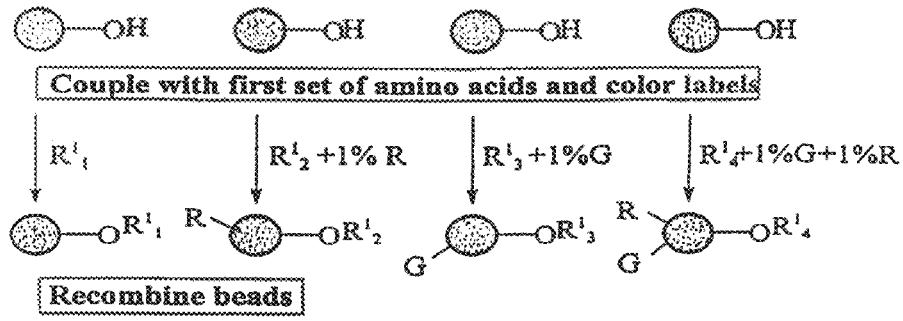
FIG. 4 is an illustration of binary color coding with fluorophores, Y, B, G and R. The example enumerate coded bead populations produced in combinatorial peptide synthesis employing reagents $R^1_1$, $R^1_2$, $R^1_3$ and $R^1_4$ in step 1 and reagents $R^2_1$, $R^2_2$, $R^2_3$ and $R^2_4$ in step 2 (see also: Table I)
Figure 4:
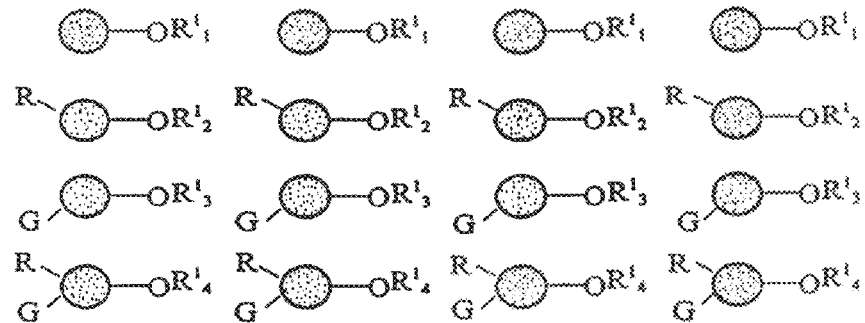
Figure 4:
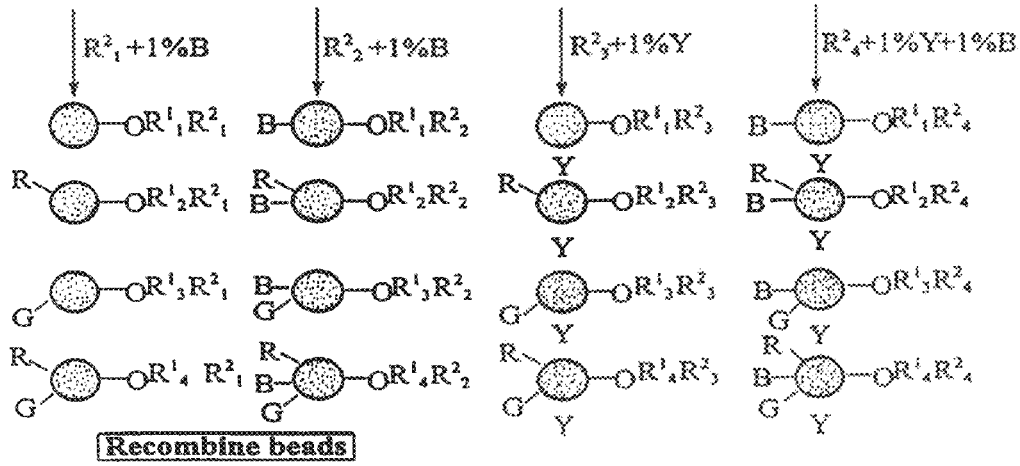

To implement the color coding strategy, the present invention takes advantage of three properties of fluorophores to construct an alphabet of fluorophore tags, namely: emission wavelength; excited-state lifetime; and emission intensity. Denoting by $m_F$ the number of available fluorophores with distinguishable emission maxima and/or excited state lifetimes, and denoting by $m_I$ the number of distinguishable intensity levels, controlled by adjusting relative quantities of fluorophores (e.g. x, 2x, 3x ... ), the size of the alphabet of fluorophore tags is $m=m_F*m_I$. The surfaces of labeled beads will display a multiplicity of distinct fluorophores (see FIG. 4). In-situ optical interrogation of these multi-colored beads serves to record emission spectra from which relative abundances of fluorophores are determined to decipher the color code, as discussed and illustrated herein.

Binary Color Codes

One rendition of this code is a binary color code (BCC) using $m_F$ fluorophores, all with $m_I=1$. This BCC will encode up to $2^{m_F}$ distinct compounds. In this BCC, the $m_F$ fluorophores could differ in excite-state lifetimes, emission maxima or both. For convenience, the following specific example uses fluorophores differing solely in their emission maxima ("colors"). The combinatorial synthesis of 16 products in two reaction steps, each using a set of N=4 reagents, would be encoded as follows:

possible sequences are represented by 4-bit strings. Thus, the sequence: "reagent $R^2_3$ in step 2, reagent $R^1_4$ in step 1" would be represented by the string 10.11 (read right to left). Using an alphabet of four fluorophores, with colors denoted by R, G, B, and Y as before, and assigned (Y, B, G, R) to represent 4-bit strings, the $2^4$ possible strings (read right to left) are encoded in BCC (m=4) as displayed in table I and in FIG. 4.

A second rendition of the color code is a binary color code using mF fluorophores with varying relative abundances and thus varying intensities at each step. The resulting eXtended binary color code (XBCC) will encode $2^{(m_F*m_I)}$ distinct compounds. For example, using an alphabet (2G, 2R, G, R) with only two distinct colors to represent 4-bit strings, $2^4$ possible strings (read right to left) are encoded in XBCC ($m_F=2$, $m_I=2$) as enumerated in Table II. In the example, deconvolution will require discrimination of four distinct intensity levels for each of the two emission bands. If N steps are involved, the number of intensity levels to be discriminated in the extended binary color code XBCC ($m_F$, $m_I$) may be as high as $N*m_F$. The attainable intensity discrimination is ultimately limited by the signal-to-noise ratio attainable in the spectral analysis of individual beads.

TABLE I

| Step 1: $R^1_1$(00) No color | $R^1_2$(01) Red | $R^1_3$(10) Green | $R^1_4$(11) Red + Green |
|---|---|---|---|
| Step 2: $R^2_1$(00) No color | $R^2_2$(01) Blue | $R^2_3$(10) Yellow | $R^2_4$(11) Yellow + Blue |

| | | | | | |
|---|---|---|---|---|---|
| $R^2_1, R^1_1$ | 00.00 NN.NN | No color | $R^2_3, R^1_1$ | 10.00 | YN.NN Y |
| $R^2_1, R^1_2$ | 00.01 NN.NR | R | $R^2_3, R^1_2$ | 10.01 | YN.NR YR |
| $R^2_1, R^1_3$ | 00.10 NN.GN | G | $R^2_3, R^1_3$ | 10.10 | YN.GN YG |
| $R^2_1, R^1_4$ | 00.11 NN.GR | GR | $R^2_3, R^1_4$ | 10.11 | YN.GR YGR |
| $R^2_2, R^1_1$ | 01.00 NB.NN | B | $R^2_4, R^1_1$ | 11.00 | YB.NN YB |
| $R^2_2, R^1_2$ | 01.01 NB.NR | BR | $R^2_4, R^1_2$ | 11.01 | YB.NR YBR |
| $R^2_2, R^1_3$ | 01.10 NB.GN | BG | $R^2_4, R^1_3$ | 11.10 | YB.GN YBG |
| $R^2_2, R^1_4$ | 01.11 NB.GR | BGR | $R^2_4, R^1_4$ | 11.11 | YB.GR YBGR |

The binary representation of four reagents is $R_1(00)$, $R^1_2(01)$, $R^1_3(10)$ and $R^1_4(11)$ for the reagents used in step 1, and $R^2_1(00)$, $R^2_2(01)$, $R^2_3(10)$ and $R^2_4(11)$ for those in step 2. As before, sequences of reaction steps correspond to concatenated binary codes, and in the example all $4^2=16$

TABLE II

| Step 1: $R^1_1$(00) No color | $R^1_2$(01) Red | $R^1_3$(10) Green | $R^1_4$(11) Red + Green |
|---|---|---|---|
| Step 2: $R^2_1$(00) No color | $R^2_2$(01) Blue | $R^2_3$(10) Yellow | $R^2_4$(11) 2Red + 2Green |

| | | | | | |
|---|---|---|---|---|---|
| $R^2_1, R^1_1$ | 00.00 NN.NN | No color | $R^2_3, R^1_1$ | 10.00 | 2GN.NN GG |
| $R^2_1, R^1_2$ | 00.01 NN.NR | R | $R^2_3, R^1_2$ | 10.01 | 2GN.NR GGR |
| $R^2_1, R^1_3$ | 00.10 NN.GN | G | $R^2_3, R^1_3$ | 10.10 | 2GN.GN GGG |
| $R^2_1, R^1_4$ | 00.11 NN.GR | GR | $R^2_3, R^1_4$ | 10.11 | 2GN.GR GGGR |
| $R^2_2, R^1_1$ | 01.00 N2R.NN | RR | $R^2_4, R^1_1$ | 11.00 | 2G2R.NN GGRR |
| $R^2_2, R^1_2$ | 01.01 N2R.NR | RRR | $R^2_4, R^1_2$ | 11.01 | 2G2R.NR GGRRR |
| $R^2_2, R^1_3$ | 01.10 N2R.GN | RRG | $R^2_4, R^1_3$ | 11.10 | 2G2R.GN GGGRR |
| $R^2_2, R^1_4$ | 01.11 N2R.GR | RRGR | $R^2_4, R^1_4$ | 11.11 | 2G2R.GR GGGRRR |

Another example describes the color-coding of products created in a combinatorial synthesis using 7 reagents in the first step, 6 reagents in each of the final two steps. Reagents are represented by binary addresses R1(001), R2(010), R3(011) . . . , R7(111); for simplicity of notation, we omit the superscript for reagents (R) used in different steps.

Let $m_F=4$ (color denoted as before) and $m_I=2$. The following XBCC based on an 8-letter alphabet (2Y, 2B, 2G, 2R, Y, B, G, R) and illustrated in Table III may be devised to encode the 7*6*6=252 synthesis products created in this synthesis. While the construction of the XBCC would require 9-bit strings to represent the full set of 8^3=512=2^9 configurations created by all possible concatenations of 3-bit strings, the actual 252 required configurations of the example can in fact be accommodated in the set of 2^8 possible 8-bit strings by making replacements of the sort indicated in the example. Thus, the reaction sequence "reagent 6 in step 3, reagent 1 in step 2, reagent 3 in step 1" is represented by the XBCC ($m_F=4$, $m_I=2$) as follows (read right to left): R6.R1.R3=2X2B.N.G=2G2RY.N.G and thus corresponds to GGGRRY.

TABLE III

| R1 | R2 | R3 | R4 | R5 | R6 | R7 |
|---|---|---|---|---|---|---|
| 000 | 001 | 010 | 011 | 100 | 101 | 110 |
| Step 1(7) N | R | G | GR | B | BR | BG NOT USED: BGR |
| Step 2(6) N | Y | 2R | 2RY | 2G | 2GY | NOT USED: 2G2R, 2G2RY |
| Step 3(6) N | 2B | 2Y | 2Y2B | 2X | 2X2B | |

Note:
By convention, make the following replacements: 2X < –2G2R, 2X2B < –2G2RY

Simple Color Codes

In contrast to the complex task of encoding reaction histories in a multi-step combinatorial synthesis, many applications require the distinction of only a limited set of chemistries. Simple color codes (SCC) can be constructed for this purpose. While not matching the encoding capacity of the corresponding binary color codes, these color codes are entirely suitable in many instances in which the chemical distinctions of interest are created in a single reaction step, such as the coupling of a diagnostic probe to a bead. Examples of such limited chemical complexity include sensing applications as well as multi-agent monitoring and diagnostics.

As with binary color codes, the construction of simple color codes takes advantage of distinguishable wavelengths, lifetimes and intensities of available fluorophores. A general version of the SCC based on a total of m fluorophores is constructed by using equal amounts of l flurophores to encode each distinct chemical species of interest, where $1 \leq l \leq m$. In this code, the set of possible combinations of colors is equivalent to the number of possible configurations, $S\_r(l,m)$, of a sample of size l drawn with replacement from a reservoir of m, $S\_R(l,m)=(m+l-1)!/l!(m-1)!$. Replacement allows for multiple instances of one color in each string.

For example, if 4 distinct fluorophores (m=4) were available, and combinations of 3 (l=3) were used—in equal relative abundances—for each distinct chemical species of interest, the generalized SCC would provide a total of 20 distinct configurations. These are listed in table IV, denoting by R, G, B and Y the colors in a 4-color alphabet. Thus, the SCC (l=3, m=4) will uniquely encode the products generated in a single step of coupling up to 20 distinct antibodies to carrier beads; each of 20 reaction vessels would receive a mixture of three fluorophores in accordance with the set listed Table IV. The presence of several known fluorophores provides the basis to invoke coincidence methods to detect and monitor weak signals and so to enhance assay sensitivity.

TABLE IV

| (R, R, R) | (G, G, G) | (B, B, B) | (Y, Y, Y) |
|---|---|---|---|
| (R, R, G) | (G, G, B) | (B, B, Y) | |
| (R, R, B) | (G, G, Y) | | |
| (R, R, Y) | | | |
| (R, G, G) | (G, B, B) | (B, Y, Y) | |
| (R, G, B) | (G, B, Y) | | |
| (R, G, Y) | | | |
| (R, B, B) | (G, Y, Y) | | |
| (R, B, Y) | | | |
| (R, Y, Y) | | | |

EXtended simple color codes (XSCC) can be constructed by varying relative abundances of fluorophores to create a set of distinguishable intensity levels for each of the fluorophore species in the alphabet. As with the XBCC, the XSCC permits control of $m_I$ intensity levels for each of $m_F$ fluorophore species in the alphabet.

Particularly easy to realize is the special case of SCC and XSCC where l=1; only a single fluorophore marks each chemical species of interest.

Further Enhancements

All color codes previously discussed herein can be further augmented by varying certain physico-chemical parameters of beads. For example, the number of encoded configurations may each be attached to a set of beads whose respective shapes, mean sizes, polarizabilities or other physico-chemical properties differ sufficiently so as to be distinguishable. By using S distinct sets of beads, the number of encoded configurations represented with XBCC(m) is increased to S*2^m.

BCC and XBCC encode chemical compound identity in terms of the relative abundances of fluorophores coupled to each bead. Accordingly, all permutations of a string of fluorophore tags are equivalent because they result in the same relative abundances. However, it has not escaped our notice that the implementation of the color code in which labeling leads to compound termination (see FIG. 3A) also retains a record of the order in which different color labels were added to each bead. Consequently, the analysis of molecular weights of labeled compounds will reveal the order in which labeling occurred.

Chemical Realization of Extended Binary Color Code

The realization of a chemical color code relies on a set ("alphabet") of chemically activated fluorophores with minimally overlapping absorption and emission spectra. We discuss here the case of the Extended Binary Color Code; other codes may be realized in analogous fashion. Although the implementation of a color code according to the present invention is illustrated herein by way of a specific family of fluorophores, the method is equally suitable for implementation with other fluorophores and chromophores whose distinctive spectral features serve to construct an alphabet of tags as described herein. An example of a suitable alphabet of six colors is provided by the CyDye™ family of indocyanine dyes, listed in FIG. 5.

The synthetic steps in this example are as follows (using standard Fmoc main-chain protection chemistry (Atherton & Sheppard, "Solid Phase Peptide Synthesis: A Practical Approach", IRL Press at Oxford University Press, Oxford, 1989, the contents are included herein by reference)).

TABLE V 1) deprotect α-amino group
2) split resin population into a small number of aliquots
3) for each resin aliquot, perform sub-stoichiometric coupling with coding CyDye activated ester; typical concentration: ≈0.001 to 0.1 mole of dye(s) per mole of α-amino
4) for each resin aliquot, perform coupling reaction with encoded amino
5) acid pool resin aliquots
6) repeat steps 1-5 for each randomized position in the amino acid sequence This procedure avoids fluorescence energy transfer between different dyes. First, labeling of any amino acid sequence as described herein will inactivate and so will terminate that sequence. Consequently, only a single dye is incorporated into any sequence and intra-sequence energy transfer is avoided. Second, low densities of dyes immobilized on the resin surface (see step 3 above) will ensure that lateral distances between labeled amino acid sequences substantially exceed the pertinent Forster radii for inter-strand fluorescent energy transfer. This is a manifestation of the well known phenomenon of "pseudo-dilution" in solid phase synthesis.

The practicability of the procedure in Table V has been demonstrated by labeling standard combination synthesis bead resins (NovaSyn TG amino resin, NovaBiochem, "Combinatorial Chemistry" Catalog, San Diego, Calif., 1997, the contents of which are included herein by reference). Specifically, we have constructed SCC(l=1, m=6) as well as XSCC(l=1, $m_F$=1, $m_f$=5) with individual dyes and with multiple dyes of the CyDye series and have shown that colors are distinguishable by fluorescence microscopy at molar ratios as low as 0.0001. In addition, we have demonstrated that the dye coupling chemistry is compatible with protein synthesis as specified in Table V.

The method of the present invention may be used to realize color encoding of amino acid or peptide combinatorial libraries, examples of which are summarized in Table VI. A suitable reporter system is an anti-β-endorphin monoclonal antibody (mAb) directed against an epitope in the form of an N-terminal amino acid sequence $N_{tes}$-YGGFL, where Y denotes tyrosine; binding of the primary anti-β-endorphin mAb to its target is detected by a cascade-blue labeled secondary anti-mouse antibody (excitation at 396 nm, emission at 410 nm).

Phase Organic Chemistry Handbook", San Diego, Calif., 1997, the contents of which are included herein by reference).

Compounds prepared by the disclosed methods have potential use as therapeutic agents in the treatment of hypertension, inflammation, and analgesia. For example, enkephalin analogues selected by the disclosed methods may be useful as analgesics. Organic compounds such as benzodiazepines useful as a muscle relaxant may also be selected by the disclosed methods.

Diagnostics and Environmental Monitoring of Multiple Agents

The method of the present invention enables a novel implementation of diagnostic assays and tests that probe simultaneously for multiple reagents or pathogens. In contrast to the spatial encoding of diagnostic panels in all prior art, random assemblies of multiple bead types, distinguishable by their respective color codes, can be mixed and handled in parallel. For example, the implementation of bead-based immunodiagnostic assay formats can take advantage of color coding as described herein to display a multiplicity of specific bead-anchored antibodies, each type assigned to a specific color code, to monitor for a multiplicity of agents in the ambient.

Figure 6A:
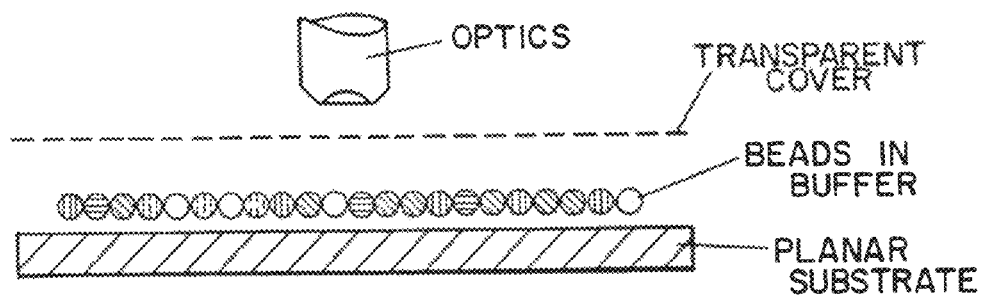
FIGS. 6A and 6B are illustrations of a random bead array encoded according to the simple color code SCC(l=1, m=5)
Figure 6B:
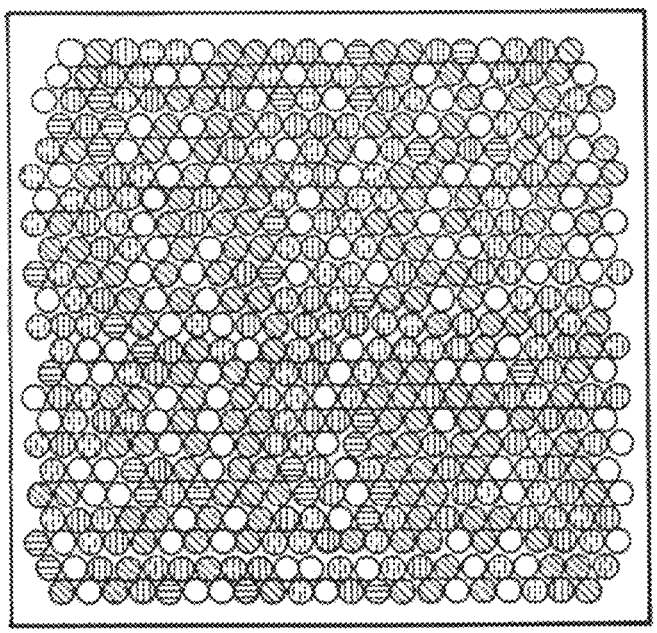
Figure 9B:
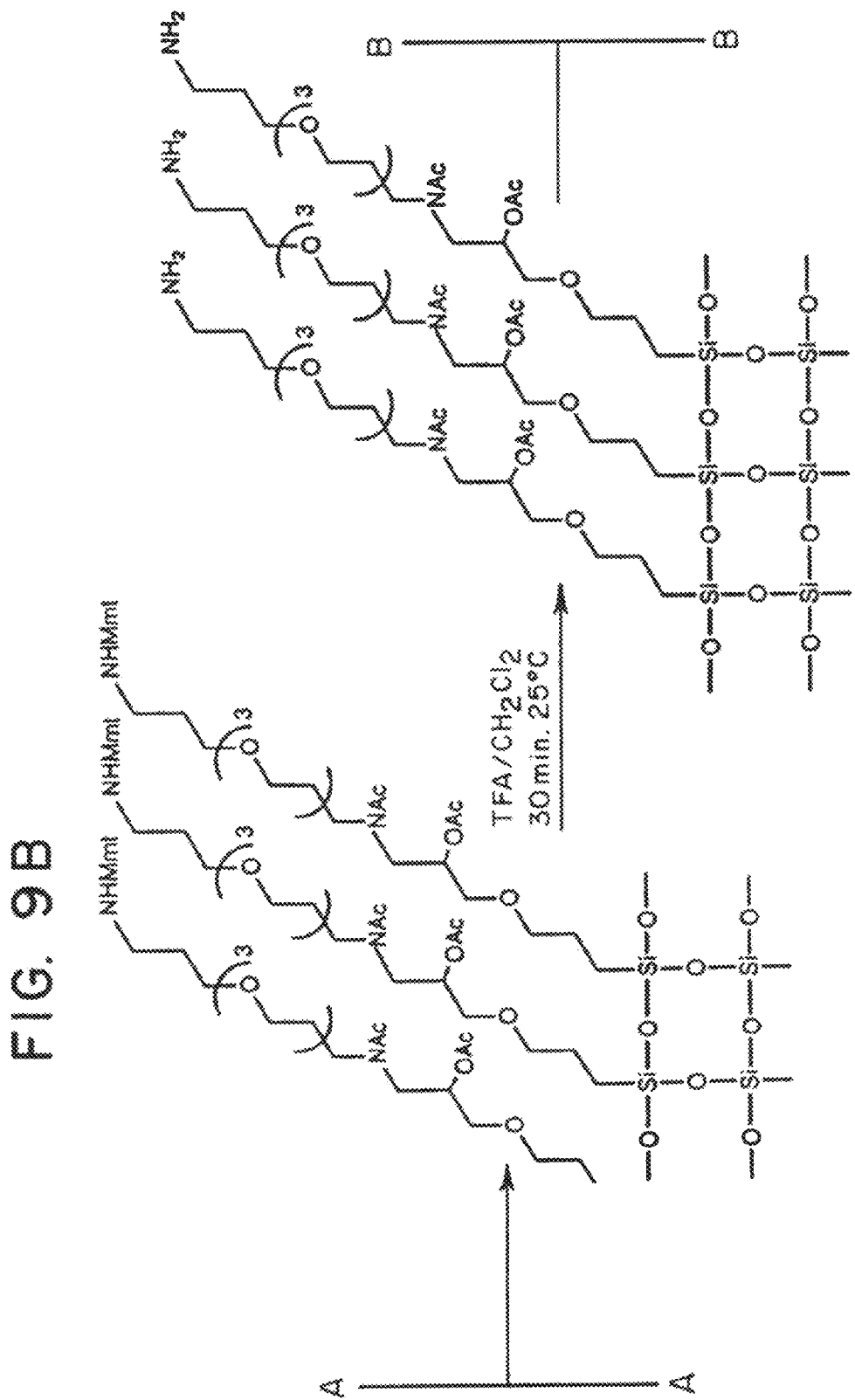
Figure 9C:
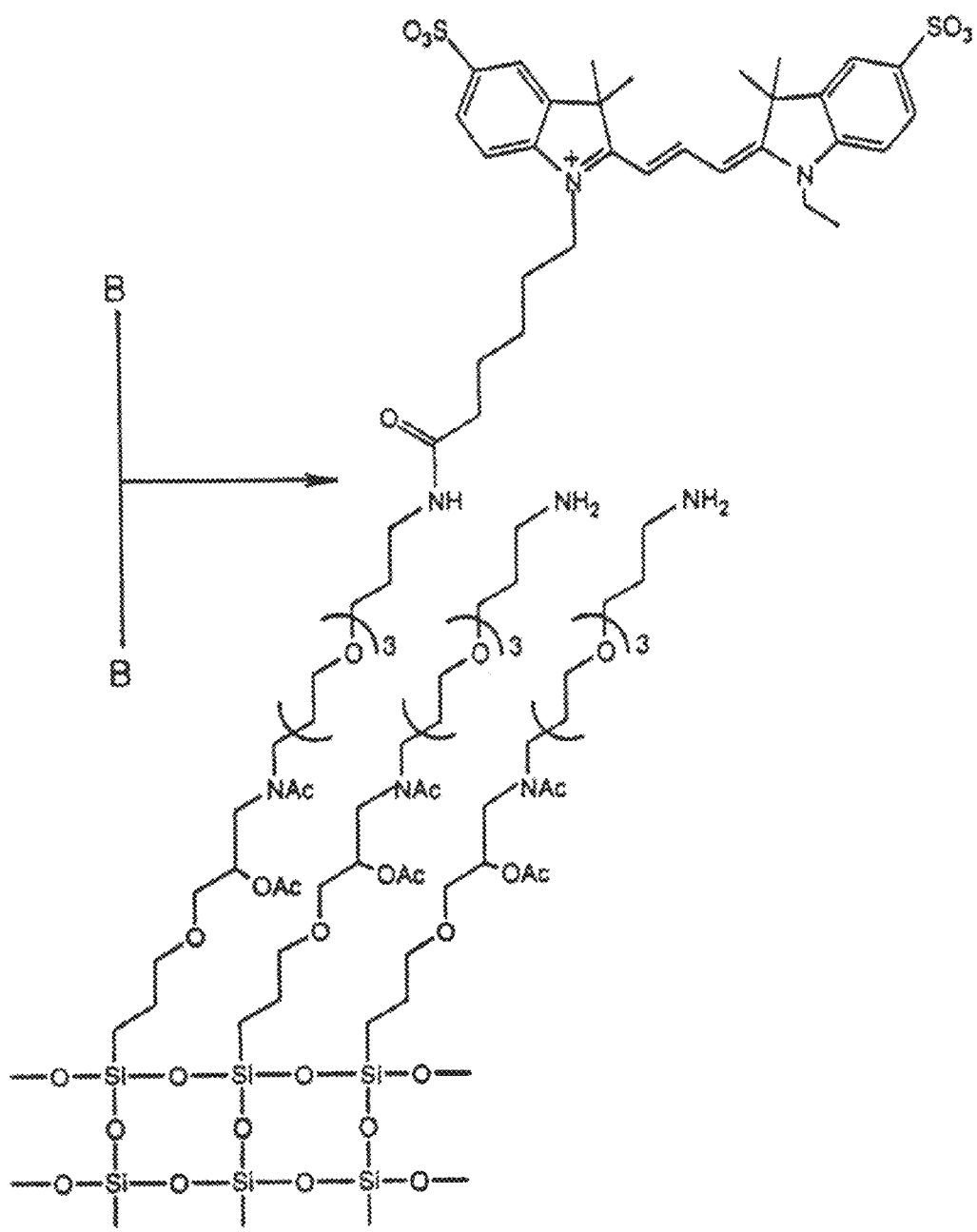

A preferred implementation of a multi-agent diagnostic assay uses random arrays of chemically encoded beads (FIG. 6). For example, the determination of blood type would require only five distinct bead types, a task that is readily addressed by the SCC (l=1, m=5). This realization of diagnostic testing and environmental monitoring devices would facilitate miniaturization, integration of multiple tests and automated operation relying on spectral read-out.

In-Situ Interrogation and Decoding of Color-Encoded Beads

The optical arrangement in FIG. 7 provides for the integration of two essential capabilities: fluorescence microscopic imaging and multi-color fluorescence analysis of individual beads. The latter serves to determine the relative abundances of several fluorophores present on the bead surface.

The use of a microscope objective of high numerical aperture (N.A.=0.7) (702) serves to maximize collection efficiency as well as spatial resolution. The principal additional components of FIG. 7 are: a long-pass filter to reject stray excitation light (704), a dichroic beam splitter (706) to

TABLE VI

| Binary Color Code (BCC) | XXGFL-βAla-BEAD | |
|---|---|---|
| bit 1: Cy2    bit 3: Cy5 | X = Gly, Ala, Tyr, Phe | 16 = 4 × 4 species created |
| bit 2: Cy3    bit 4: Cy7 | | 16 = 2^4 species created |
| 2-Level eXtended BCC | ZXXFL-βAla-BE AD | 252 = 7 * 6 * 6 species created |
| bit 1: Cy2    bit 5: Cy5 | Z = Gly, Ala, Glu, Lys, Phe, | 256 = 2^8 species created |
| bit 2: 2 * Cy2   bit 6: 2 * Cy5 | Tyr, D-Tyr | |
| bit 3: Cy3    bit 7: Cy7 | X = Gly, Ala, Glu, Lys, Phe, | |
| bit 4: 2 * Cy3   bit 8: 2 * Cy7 | Tyr | |
| 3-Level eXtended BCC | XXXXL-βAla-BEAD | 4096 = 8^4 species created |
| bit 1: Cy2    bit 7: Cy5 | X = Gly, Ala, Ser, Asn, Glu, | 4096 = 2^12 species created |
| bit 2: 2 * Cy2   bit 8: 2 * Cy5 | Lys, Phe, Tyr | |
| bit 3: 4 * Cy2   bit 9: 4 * Cy5 | | |
| bit 4: Cy3    bit 10: Cy7 | | |
| bit 5: 2 * Cy3   bit 11: 2 * Cy7 | | |
| bit 6: 4 * Cy3   bit 12: 4 * Cy7 | | |

Although the method of the present invention is illustrated by making reference to peptides and peptide precursors, the method is equally suitable with any other chemical precursors and compound classes that have been created via DCR combinatorial synthesis (Calbiochem-NovaBiochem, "Solid separate beams for image formation by the field lens (708) and spectral analysis via focusing of the light (by lens 710) on the slit aperture of a grating monochromator (712) or, alternatively (not shown), on the entrance pupil of an optical fiber that is coupled to a grating monochromator; multi-color spectra are recorded by a CCD array (714). Infinity-corrected optical components offer convenience of implementation.

While simple long pass filters have been employed in DNA sequencing applications to reject stray excitation light supplied at a single wavelength, interference filters can be designed to provide multiple narrow (10 nm) pass-bands at several emission wavelengths characteristic of the CyDye family of fluorophores discussed herein. Similar fabrication techniques may be applied to the dichroic mirror. These considerations are particularly relevant to an epi-fluorescence geometry, a special case of reflection microscopy.

Among the suitable instrumental realizations of recording spectral information from individual color-encoded beads or collections of color-encoded beads are flow cytometric analysis and multi-spectral imaging. The latter permits the collection of spectral information from individual or multiple beads in the field of view of a microscope or other imaging device, as considered in FIG. 7.

Methods suitable for multi-spectral imaging include: multiplexing of distinct wavelengths of incident and emitted light and illumination with a superposition of multiple wavelengths, followed by dispersive imaging by means of a grating or prism (see FIG. 7) or followed by interferometric analysis of emitted light.

The first method is readily implemented using matching optical pass-band filters; these are mounted in filterwheels and positioned in incident and emitted light paths of a microscope. The synchronized rotation of the two filterwheels will insert matching pairs of excitation and emission filters (a reflective geometry will also require a suitable dichroic mirror) into the light path, producing a repeating series of images at each of the distinct wavelengths selected one of the filter/mirror combination. This principle is realized, for example, in the Fluorescence Imaging MicroSpectrophotometer developed by Kairos Scientific (Santa Clara, Calif.).

In the second method, distinct wavelengths for illumination are produced by a multi-pass band filter/mirror combination; a prism is inserted into the output path. This configuration facilitates the imultaneous spectral analysis of multiple beads located in a rectangular slice of the field of view of the microscope. Light emitted from beads within this slice is imaged onto the entrance slit of the prism and is decomposed into its spectral components. This principle is realized in the PARISS Imaging Spectrometer attachment developed by LightForm (Belle Meade, N.J.). In the third method, light from the entire field of view is analyzed inteferometrically: a pellicle beamsplitter in the output path produces two (coherent) light beams which are reflected by a mirror and recombined. As the beamsplitter is rotated, a small difference in pathlength is introduced between the two light beams, resulting in interference fringes as the two beams are recombined. These fringes contain the entire spectral information contained in the light emitted from the field of view of a microscope (Garin et al, Bioimaging 4, 65-72 (1996)). That is, as the beamsplitter is rotated, a continuous spetrum is generated for every position within the field of view, resulting in a three-dimensional representation of the data. This principle is realized in the SpectraCube system developed and marketed by Applied Spectral Imaging (Carlsbad, Calif.). In contrast to the first method, the second and third methods generate a continuous spectrum, facilitating spectral classification of overlapping emission bands.

The arrangements in FIG. 8 provide for additional flexibility in rejecting stray light by spatially separating incident light and emitted light collection in transmission and rejection microscopy, as illustrated in FIGS. 8A and 8B, respectively. In addition, the use of specially deigned multi-pass band interference filters in the output light path is again an option.

The demands on the sensitivity of the multi-color fluorescence detection system derive from the number of fluorophores of each color expected to be present on a selected bead. A bead of radius R and surface area $A=4\pi R^2$ will accommodate up to $N=A/a$ molecules of molecular area a, or $N^*=xN$ fluorophores. With $a=30$ A and $0.01<x<0.1$, a bead of 10 µm diameter may carry $10^7 \leq N^* \leq 10^8$ flurophores. For comparison, imaging of small circular domains of 10 µm diameter within a monomolecular film composed of a phospholipid containing 1 mole % of a fluorescent analog and confined to an air-water interface, is based on a comparable number of fluorophores and is readily accomplished using silicon-intensified target (SIT) camera technology. The refractive property of beads in aqueous solution will further enhance the light collection efficiency of the entire system.

In-Situ Interrogation and Decoding of Color-Encoded Bead Arrays

The present invention provides a methodology for color-encoding of beads and describes a method and apparatus for in-situ interrogation and decoding of color-encoded beads and collections of beads by multi-color fluorescence imaging and spectral analysis. This method is compatible with all bead assay formats described to date, as discussed herein.

A preferred format providing a particularly efficient realization of bead assays on the basis of the methods and apparatus of the present invention involves planar beads arrays. This format facilitates highly parallel screening of enzyme activity, receptor-ligand binding, antibody-antigen recognition as well as DNA or RNA hybridization, etc. Thus, a close-packed array of 100 µm diameter beads can contain of the order of $10^4$ beads in an area of only 1 cm$^2$, permitting the examination of up to $10^4$ compounds/cm$^2$ in a single pass. The instantaneous determination of chemical identities enables the efficient implementation of reiterative screening in which multiple copies of each bead type are examined to establish a statistically robust ranking of compounds producing positive assay scores. Furthermore, the implementation of the present invention in a planar bead array format lends itself to automation. Automated operation would entail the preparation of planar bead arrays, followed by fluorescence imaging of the array to locate beads that are to be subjected to spectral analysis and on-line decoding. The intrinsic detection sensitivity of fluorescence, demonstrated at the level of detecting single fluorophores, makes it possible to substantially reduce the size of synthesis beads. This in turn facilitates miniaturization and containment within an enclosed system, with its attendant benefits of reducing the requisite quantity of synthesized compound and the amount of reagents consumed in the course of screening.

One method of forming planar bead arrays is to rely on gravity-driven settling of beads from suspension to produce a (static) layer of beads or arrangement of bead clusters on a planar substrate. A second method employs dynamic planar bead arrays that are formed adjacent to planar surfaces and manipulated in-situ under external control, for example by Light-controlled Electrokinetic Assembly of Particles near Surfaces (LEAPS). LEAPS is a technology that provides the capability to form dynamic planar bead arrays in aqueous solution on cue and to place and maintain them in a designated area of a planar electrode surface, as set forth in the copending PCT application filed Apr. 24, 1997, entitled "Light Controlled Electrokinetic Assembly of Particles Near Surfaces", based on U.S. Provisional Application Ser. No. 60/016,642, filed Apr. 25, 1996, which is incorporated by reference herein.

Dynamic planar bead arrays provide additional advantages in the realization of automated screening assays in a miniaturized, contained environment. Bead suspensions from a synthesis pool will be loaded into a "sandwich" flow cell where planar bead arrays are formed adjacent to the planar walls of cell; screening assays will be performed in planar array format to identify lead compounds without the need of a time-consuming and error-prone step of physical separation; following completion of the scheduled assays, bead arrays will be disassembled and the bead suspension discharged to ready the flow cell for another cycle. In the example, a redundancy of 10, i.e., the presence of 10 copies of beads of identical type and color code, would still facilitate screening of 1000 compounds at a time, but would considerably enhance the quality of any pharmacokinetic characterization. The benefits of miniaturization would be enhanced by the use of small synthesis beads. Chemically and physically well defined beads in the requisite size range (10 µm diameter) are available from many commercial sources. They are readily manipulated by LEAPS to form dynamic planar bead arrays of high density. This ensures that screening assays may be performed in a highly parallel format on a large number of samples, and this in turn provides the basis for highly reiterative screening and for a robust pharmacokinetic characterization of potential lead compounds.

The present invention will be better understood from the Experimental Details which follow. However, one skilled in the art will readily appreciate that the specific methods and results discussed are merely illustrative of the invention as described in the claims which follow thereafter.

Example 1

1. Color-Encoded PEG-Polystyrene Microspheres
a. Preparation of Color-Encoded PEG-Polystyrene Microspheres
(1) Cy2 (Ex=489 nm, Em=506 nm)-Color-Encoded PEG-Polystyrene Microspheres:

50 mg of NovaSyn TG amino microspheres (NovaBiochem; 130µ diameter, 15 µmol amine) were equilibrated in 10 ml DMF 30 min at 25° C. The supernatant was removed by filtration, and 100 µl DMF, 1 µl TEA and 15 µl 1 mM Cy2-bisfunctional NHS-ester (Amersham; 15 nmol) were added in DMF. The reaction mixture was shaken 1 h at 25° C., 2 µl (20 µmole) n-butylamine was added, and the reaction mixture was shaken a further 30 min at 25° C. The supernatant was removed, and microspheres were washed twice with 5 ml DMF, rinsed twice with 5 ml chloroform and dried in vacuo.
(2) Cy3 (Ex=550 nm, Em=570 nm)-Color-Encoded PEG-Polystyrene Microspheres:

This preparation was identical to (1) except that, in parallel reactions, 15 µl of 0.001, 0.01, 0.1, and 1 mM Cy3-monofunctional NHS-ester (Amersham; 0.15, 1.5, and 15 nmol) were used, and the n-butylamine step was omitted.
(3) Cy3.5 (Ex=581 nm, Em=596 nm)-Color-Encoded PEG-Polystyrene Microspheres:

This preparation was identical to (1) except that 15 µl of 1 mM Cy3.5-monofunctional NHS-ester (Amersham; 15 nmol) was used, and the n-butylamine was step omitted.

(4) Cy5 (Ex=649 nm, Em=670 nm)-Color-Encoded PEG-Polystyrene Microspheres:

This preparation was identical to (1) except that 15 µl of 1 mM Cy5-monofunctional NHS-ester (Amersham; 15 nmol) was used, and the n-butylamine step was omitted.
(5) Cy5.5 (Ex=675 nm, Em=694 nm)-Color-Encoded PEG-Polystyrene Microspheres:

This preparation was identical to (1) except that 15 µl of 1 mM Cy5.5-monofunctional NHS-ester (Amersham; 15 nmol) was used, and the n-butylamine step was omitted.
(6) Cy7 (Ex=743 nm, Em=767 nm)-Color-Encoded PEG-Polystyrene Microspheres:

This preparation was identical to (1) except that 15 µl of 1 mM Cy7-bisfunctional NHS-ester (Amersham; 15 nmol) was used.
(7) Cy3/Cy5-Color-Encoded PEG-Polystyrene Microspheres:

This preparation was identical to (1) except that both Cy3-monofunctional NHS-ester and Cy5-monfunctional NHS-ester were added (15 µl of 1 mM stock each), and the n-butylamine step was omitted.
(8) Cy2/Cy3/Cy5/Cy7-Color-Encoded PEG-Polystyrene Microspheres:

This preparation was identical to (1) except that Cy2-bisfunctional NHS-ester, Cy3-monofunctional NHS-ester, Cy5-monofunctional NHS-ester, and Cy7-bisfunctional NHS-ester were added (15 µl of 1 mM stock each).
b. Stability of Cy3-Encoded PEG-Polystyrene Microspheres to Solid-Phase Peptide Synthesis Conditions.

Cy3-encoded PEG-polystyrene microspheres were subjected to one cycle of solid-phase peptide synthesis. 50 mg microspheres and 5 mg Fmoc(Lys)Boc-OBT [prepared by reacting 94 mg Fmoc(Lys)Boc-OH (NovaBiochem; 0.2 mmol), 48 mg DCC (Aldrich; 0.22 mmol) and 27 mg HOBT (Aldrich; 0.2 mmol) in 2 ml DMF for 0.5 h at 25° C., centrifuging at 2000×g 5 min at 25° C., and using 100 µl of the supernatant) in 100 µl DMF were shaken 0.5 h at 25° C.

The microspheres were filtered, suspended in 100 µl 20% piperidine in DMF 15 min at 25° C., washed twice with 5 ml CHCl$_3$, and dried. The UV/VIS absorbance and fluoresence properties of the Cy3-encoded PEG-polystyrene microspheres were unchanged.
c. Optical Properties of Color-Encoded PEG-Polystyrene Microspheres Microspheres examined for their optical properties included:

Cy3 (ex=550 nm, em=570 nm)-color-encoded PEG-polystyrene microspheres of four different intensity levels, prepared as described in section a-(2) above by reacting beads with 0.001, 0.01, 0.1 and 1 mM Cy3, are denoted b3-0001, b3-001, b3-01 and b3-1, respectively; as a group, all the Cy3-encoded PEG-polystyrene microspheres are denoted b3-x.

Cy5 (ex=649 nm, em=670 nm)-color-encoded PEG-polystyrene microspheres, prepared as described in section a-(2) above by reacting beads with 1 mM Cy5, are denoted b5-1; Cy3/Cy5-color-encoded PEG-polystyrene microspheres, prepared as described in section a-(2) above by reacting beads with 1 mM Cy3/Cy5, are denoted b35-1.

An aliqout of dried microspheres was suspended in DMF and dispersed on a silicon wafer; DMF was evaporated by gentle heating. All subsequent observations were made in air.
(1) Fluorescence Imaging Observations were made with a Zeiss UEM microscope equipped for epifluorescence; combinations of excitation filter/dichroic mirror/emission filter designed for Cy3 and Cy5 (Chroma Technologies, Brattleboro, Vt.) were used in conjunction with a 100 W halogen illuminator and objectives of 10×, 25× and 40× magnification. Optionally, images were recorded with a SIT camera (Cohu, San Diego, Calif.).

All microspheres displayed a bright circumferential "ring" of high intensity, corresponding to ≤5% of the particle diameter, suggesting that label was associated primarily with the surface, rather than the interior, of each particle. Even the dimmest particles, of type b3-0001, were readily observable using a 25×/0.45 NA objective and the SIT camera. Microspheres of type b3-0001 appeared dimmer than did microspheres of type b3-001, although by less than the expected factor of 10. This phenomenon remains to be explored, but may indicate fluorescence quenching. Any given set of Cy3-encoded microspheres displayed particle-to-particle variations in color: some particles appeared orange, others yellow of type b5-1 appeared bright red.

(2) Fluorescence Spectra

To demonstrate the feasibility of in-situ interrogation of color-encoded microspheres, fluorescence spectra were recorded from individual color-encoded PEG-polystyrene microspheres by means of a PARISS™ imaging spectrophoto-meter (prototype supplied by LightForm, Belle Meade, N.J.) with 50 µm wide entrance slit, curved prism and room-temperature CCD array capable of on-chip integration. The instrument was mounted to the camera port of a Zeiss UEM microscope. In this configuration, multiple beads which are lined up along the long dimension of the projected slit can be imaged and spectrally analyzed. Only an approximate wavelength calibration was performed.

Spectra displaying fluorescence intensity as a function of wavelength were obtained separately for Cy3- and for Cy5-encoded microspheres and showed the following spectral characteristics:

b3-x: spectra were obtained for all types of particles; specific features included: for b3-0001:

signal-to-noise (S/N)≈2, signal-to-background (S/B)≈1.5; for b3-001: S/N≈4, S/B≈2 (with a CCD integration time of approximately 10 s); smoothing clearly revealed characteristic spectral features; for b3-1: S/N>10;

b5-1: very clean spectra were recorded, all with a slight skew toward high wavelength;

b35-1: very clean spectra of either label were recorded, switching between appropriate filters to simulate filter wheel operation. At this concentration, spectra (taken with 10-times shorter integration time than that used for b3-01 and b3-001) displayed no discernible noise.

2. Color-Encoded Macroporous Polystyrene Microspheres a. Preparation of Color-Encoded Macroporous Polystyrene Microspheres 50 mg Amino-Biolinker-PMI-1000 amino oligoethylene glycol-functionalized macroporous polystyrene microspheres (Solid Phase Sciences; 35µ diameter, 7 µmol amine) were equilibrated in 2 ml DMF 20 min at 25° C. The supernatant was removed by filtration, and 100 µl DMF, 1 µl TEA, and 70 µl 1 mM Cy3-monofunctional NHS-ester (Amersham; 70 nmol) were added. After 1 hr at 25° C. with shaking, the supernatant was removed by filtration, and the microspheres were washed twice with 5 ml DMF, washed twice with 5 ml CHCl$_3$, and dried in vacuo.

b. Optical Properties of Color-Encoded Macroporous Polystyrene Microspheres

Visual inspection using the configuration described under Example 1, revealed substantial bead-to-bead variations in fluorescence intensity.

3. Color-Encoded Solid Glass Microspheres ("Pelicular Microspheres")

a. Preparation of Color-Encoded Pelicular Microspheres (1) Epoxide-Functionalized Pelicular Microspheres:

4 g solid sodalime glass microspheres (Duke Scientific; 40±3µ diameter; 4.8×10$^7$ microspheres), 7 ml xylene, 2.34 ml 3-glycidoxypropyltrimethoxysilane (Aldrich; 1 mmol) and 0.117 ml diisopropylethylamine (Aldrich; 0.7 mmol) were shaken 18 h at 80° C. Upon cooling to room temperature, microspheres were filtered, washed with 40 ml methanol, washed with 40 ml diethyl ether, and dried in vacuo.

(2) MMT-NH-PEG-Functionalized Pelicular Microspheres:

Microspheres from (1) were suspended in a solution of 200 mg mono-MMT-1,13-trioxotridecadiamine [0.4 mmol; prepared by mixing 7 g MMT-Cl (Aldrich; 23 mmol) and 11.3 ml 4,7,10-trioxa-1,13-tridecanediamine (Aldrich; 51 mmol) in 150 ml 1:1:1 methylene chloride:pyridine:acetonitrile for 18 h at 25° C., then isolating the required adduct by chromatography on silica gel) in 6 ml xylene. Approximately 10 mg sodium hydride (Aldrich; 0.4 mmol) was added, and the suspension shaken 18 h at 40° C. under a drying tube.

Microspheres then were filtered and successively washed with 20 ml methanol, 10 ml water, 20 ml methanol, and 20 ml chloroform, and dried in vacuo.

Dried microspheres were capped by reaction with 5% acetic anhydride, 5% 2,6-lutidine, 8% N-methylimidazole in 10 ml tetrahydrofuran 1 h at 25° C. with shaking, successively washed in 2×5 ml methanol, 2×5 ml chloroform, and 2×5 ml diethyl ether, and dried in vacuo.

(3) H$_2$N-PEG-Functionalized Pelicular Microspheres:

Microspheres from (2) were treated with 1 ml 3% TFA in CH$_2$Cl$_2$ 0.5 h at 25° C. with shaking. Based on quantitation of released monomethoxy trityl cation ($\epsilon_{478}$=3.47×10$^4$ M$^{-1}$ cm$^{-1}$) the loading densities of H$_2$N-PEG were as follows:

15 fmol H$_2$N-PEG per microsphere
1.1×10$^{10}$ molecules H$_2$N-PEG per microsphere
0.022 molecule H$_2$N-PEG per Å$^2$ Assuming ≈0.04 available silanol groups per Å$^2$ of sodalime glass, the grafting efficiency was ≈50%.

(4) Color-Encoded Peg-Functionalized Pelicular Microspheres:

To 20 mg of H$_2$N-PEG-functionalized pelicular microspheres (4.2 nmol amine), were added 97 µl DMF, 2 µl TEA, and 0.8 µl 1 mM Cy3-monofunctional NHS-ester (Amersham; 0.8 nmol), and the resulting suspension was shaken for 18 h at 25° C. Microspheres then were filtered and washed successively with 5 ml DMF, 5 ml methanol, 5 ml chloroform, and 5 ml diethyl ether, and dried in vacuo.

Based on quantitation of consumed Cy3-monofunctional NHS-ester ($\epsilon_{552}$=1.5×10$^5$ M-1 cm$^{-1}$) the loading of Cy3 densities were as follows:

1 fmol Cy3 per microsphere
6×10$^8$ molecules Cy3 per microsphere
0.001 molecule Cy3 per Å$^2$
0.07 molecule Cy3 per molecule available H$_2$N-PEG b. Optical Properties of Cy3-Encoded Peg-Functionalized Pelicular Microspheres:

Visual inspection using the configuration described under Example 1, revealed uniformly fluorescent microspheres.

What is claimed is:

1. A method of identifying a compound of interest in a library of compounds, each of said compounds being bound to a solid support and being produced by a unique reaction series composed of N reaction steps, wherein N is 1, and wherein each compound is produced from components which are independently the same or different, the method comprising:

(a) dividing a population of solid support into M batches, wherein M is an integer greater than 1;

(b) reacting each of the M batches of solid support with a component, so that the component forms a bond with the solid support;

(c) adding to one or more batches, prior to (b), concurrently with (b), or subsequently to (b), one or more tag(s), each tag able to be attached to the solid support and able to be identified by optical interrogation, wherein said one or more tag(s) constitutes a code, which code is uniquely associated with a compound and a corresponding reaction sequence and is determined by optical interrogation;

(d) recombining all of said M batches after (b) and (c);

(e) repeating (a) to (d) for N−1 times to produce a library of compounds;

(f) performing an assay capable of indicating that any compound in the library has a property of interest; and (g) decoding the code composed of one or more tag(s) to identify the compound associated with the code, wherein the decoding step is carried out without isolating the solid support comprising the compound having the property of interest from the other solid supports and without detaching any of the tag(s) from the solid support comprising the compound having the property of interest and wherein said decoding step comprises in-situ optical interrogation of the tag(s).

2. A method of identifying a compound having a selected property of interest in a library of compounds, each of said compounds being bound to its respective solid support, and being produced by a unique reaction series composed of N reaction steps, wherein each compound is prepared from a component, and N is an integer from at least 1 to about 100, which comprises:

a) dividing a population of solid supports having at least one OH functional group at the surface of said solid support, into M batches, wherein M is an integer from at least 2 to about 25;

b) coupling the M batches of solid support in a set of at least one reaction respectively with M different components so as to form a bond with the solid support via said first functional group, said components being independently optionally protected;

c) adding to each batch, optionally prior to coupling step b), concurrently therewith, or subsequently to step b), from 0.001 to 0.1 molar equivalent of a spectrally distinguishable fluorophore tag associated uniquely with each component, said tag being identified by its characteristic excitation wavelength(s), emission wavelength(s), excited state lifetime and emission intensity, said tag being activated so as to be capable of forming either a direct bond to the surface of the solid support, optionally via a second functional group which is optionally protected and may be the same as or different from the first functional group bonded to the component, or an indirect bond via a $C_1$-$C_9$ linear or branched alkyl linker moiety which is optionally interrupted by at least one oxygen or nitrogen atom or a carbonyl, (C=O)NH or NH(C=O) moiety, wherein when said second functional group is protected, said functional group is deprotected prior to forming said direct or indirect bond, said linker being bonded to the second functional group at the surface of the solid support;

d) optionally recombining all M batches, said recombining step optionally being subsequent to step e);

e) performing an assay capable of indicating that any compound in the library either while bound to or cleaved from its solid support has the property of interest;

f) collecting spectral fluorescence data for each respective solid support so as to determine respective relative abundances of the fluorophore tags bound thereto;

g) analyzing the collected spectral fluorescence data by comparing the respective relative abundances of the fluorophore tags determined in step f) so as to determine the unique reaction series for the compound, thereby identifying the compound having the property of interest.

3. A method of identifying a compound of interest in a library of compounds, each of said compounds being bound to its respective solid support and produced by a unique reaction series composed of N reaction steps, wherein N is an integer from at least 1 to about 100, and wherein each compound is produced from components which are independently the same or different, said method comprising:

(a) dividing a population of solid supports having at least one OH functional group at the surface of said solid support, into M batches, wherein M is an integer from at least 2 to about 25;

(b) reacting each of the M batches of solid support with a component, so that the component forms a bond with the solid support via the functional group, the component being independently protected or unprotected;

(c) adding to each batch, prior to coupling step b), concurrently therewith, or subsequently to step b), from 0.001 to 0.1 molar equivalent of a spectrally distinguishable fluorophore tag uniquely associated with each component and capable of forming a bond to the solid support or to the component, wherein said fluorophore tag represents a bit of binary code and comprises zero, one, or more than one fluorescent dye(s), said dye(s) being spectrally distinguishable by excitation wavelength, emission wavelength, excited-state lifetime or emission intensity;

(d) recombining all of said M batches after the coupling and the tagging step;

(e) repeating steps (a) to (d) for N−1 times, or repeating steps (a) to (d) for N−2 times followed by repeating steps (a) to (c) once, to produce a library of compounds;

(f) performing an assay capable of indicating that any compound in the library has a property of interest; and (g) identifying the compound having the property of interest by optically interrogating the fluorophore tag(s) bound to the solid support on which the compound having the property of interest was produced, said optical interrogation being carried out without isolating the solid support of interest from other solid supports.

4. The method of claim 1, wherein said tag is a fluorescent tag, and wherein said fluorescent tag being spectrally distinguishable by excitation wavelength, emission wavelength, excited-state lifetime, or emission intensity.

* * * * *